(12) United States Patent
Sengun et al.

(10) Patent No.: US 10,485,652 B2
(45) Date of Patent: Nov. 26, 2019

(54) FLEXIBLE IMPLANT WITH ADJUSTABLE COILS

(71) Applicant: DePuy Synthes Products, Inc., Raynham, MA (US)

(72) Inventors: Mehmet Ziya Sengun, Canton, MA (US); Jacob A. Marks, Mansfield, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 38 days.

(21) Appl. No.: 15/863,022

(22) Filed: Jan. 5, 2018

(65) Prior Publication Data

US 2018/0125638 A1     May 10, 2018

Related U.S. Application Data

(62) Division of application No. 15/001,184, filed on Jan. 19, 2016, now Pat. No. 9,888,998.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0459* (2013.01); *A61F 2002/0823* (2013.01); *A61F 2002/0835* (2013.01); *A61F 2002/0852* (2013.01)

(58) Field of Classification Search
CPC .. A61F 2/08; A61F 2/0811; A61F 2002/0823; A61F 2002/0817
See application file for complete search history.

(56) References Cited

U.S. PATENT DOCUMENTS

| | | | |
|---|---|---|---|
| 7,749,250 | B2 | 7/2010 | Stone et al. |
| 7,905,903 | B2 | 3/2011 | Stone et al. |
| 7,959,650 | B2 | 6/2011 | Kaiser et al. |
| 9,060,763 | B2 | 6/2015 | Sengun |
| 9,603,591 | B2 * | 3/2017 | Denham ............ A61B 17/0401 |
| 9,888,998 | B2 | 2/2018 | Sengun et al. |
| 2008/0177304 | A1 | 7/2008 | Westra et al. |
| 2011/0022083 | A1 | 1/2011 | DiMatteo et al. |
| 2011/0022084 | A1 | 1/2011 | Sengun et al. |

(Continued)

OTHER PUBLICATIONS

International Search Report for Application No. PCT/US2017/013089, dated Apr. 4, 2017 (6 pages).

*Primary Examiner* — Jason-Dennis N Stewart

(57) ABSTRACT

Devices and methods for securing a graft with respect to bone are provided. One exemplary embodiment of a surgical implant includes a flexible filament body and a suture filament or repair construct that extends through the filament body at multiple locations. The repair construct is formed into one or more coils, which can receive a graft. The flexible filament body can be configured to be actuated between unstressed and anchoring configurations, the latter of which sets a location of the suture filament, and associated graft, in a bone tunnel. More particularly, the flexible filament body can ball up, or become denser, to a size that cannot pass into the bone tunnel in which the suture filament holding the graft is disposed. The present disclosure also provides for feedback units to assist a surgeon in knowing a location of the implant. Further, other exemplary devices and methods are provided.

23 Claims, 16 Drawing Sheets

(56) References Cited

U.S. PATENT DOCUMENTS

| | | |
|---|---|---|
| 2012/0130424 A1 | 5/2012 | Sengun et al. |
| 2012/0197271 A1 | 8/2012 | Astorino et al. |
| 2012/0290004 A1 | 11/2012 | Lombardo et al. |
| 2013/0035722 A1 | 2/2013 | McDevitt et al. |
| 2013/0123810 A1 | 5/2013 | Brown et al. |
| 2014/0163614 A1* | 6/2014 | Denham ............ A61B 17/0401 606/228 |
| 2014/0257346 A1 | 9/2014 | Sengun et al. |
| 2014/0336703 A1 | 11/2014 | Sengun et al. |
| 2015/0038992 A1 | 2/2015 | DiMatteo et al. |
| 2015/0157449 A1* | 6/2015 | Gustafson ............ A61F 2/0811 606/145 |
| 2017/0202658 A1 | 7/2017 | Sengun et al. |

* cited by examiner

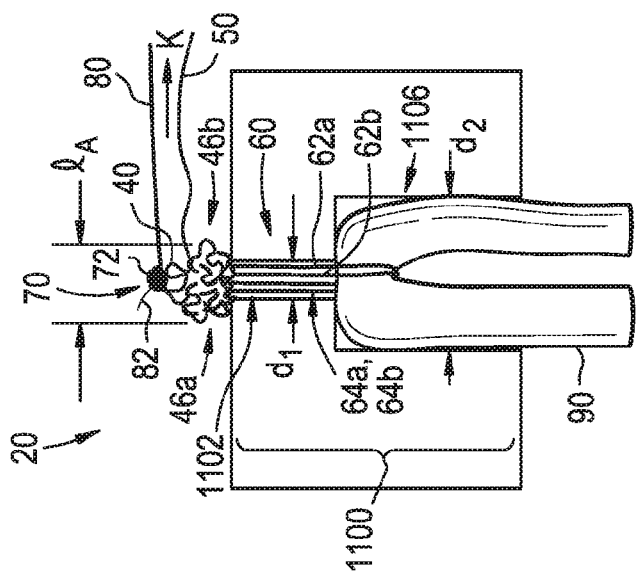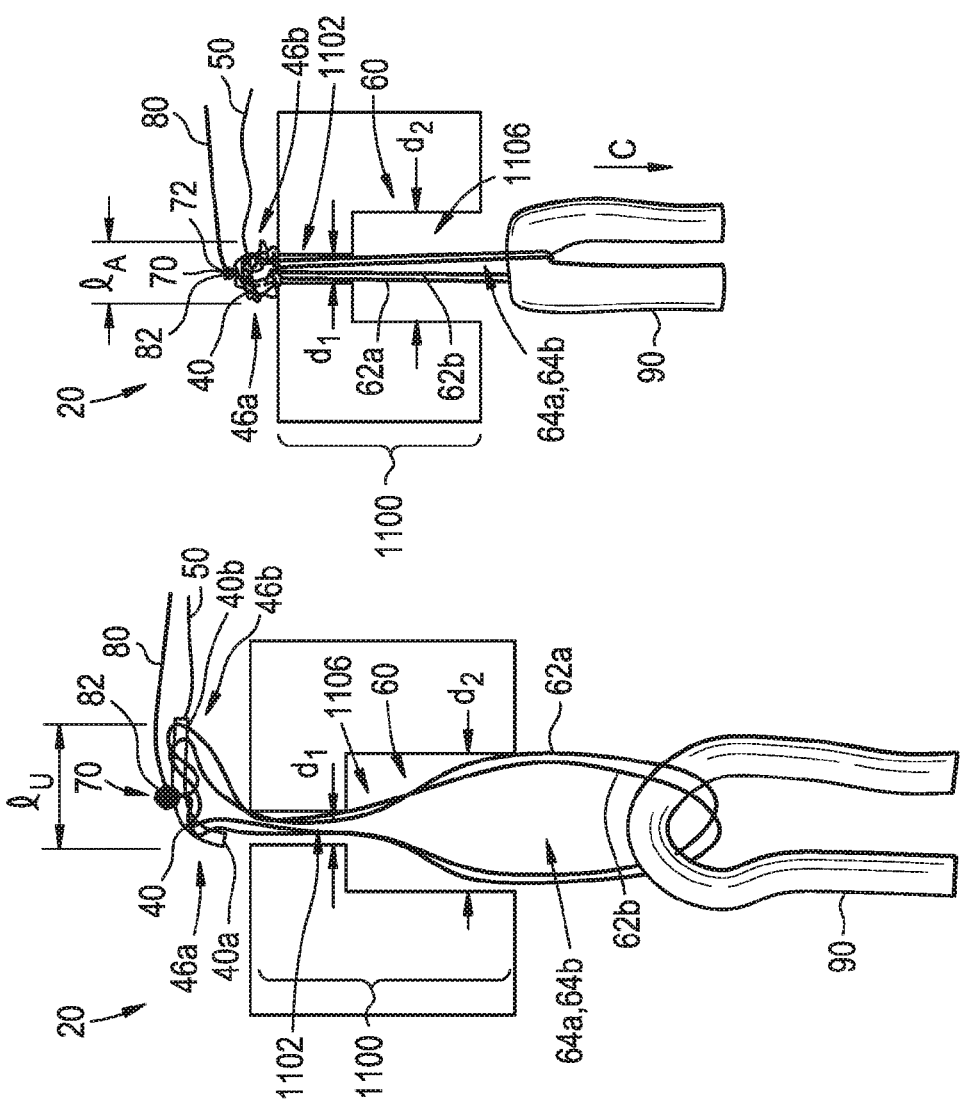

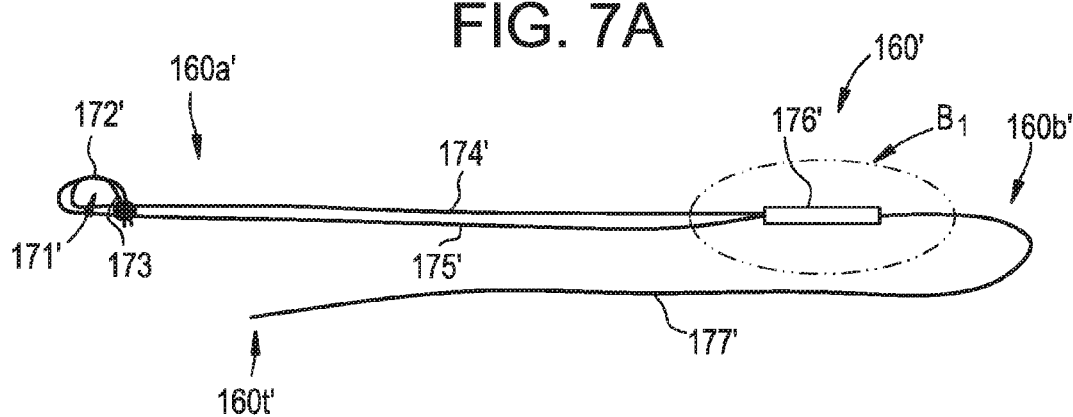
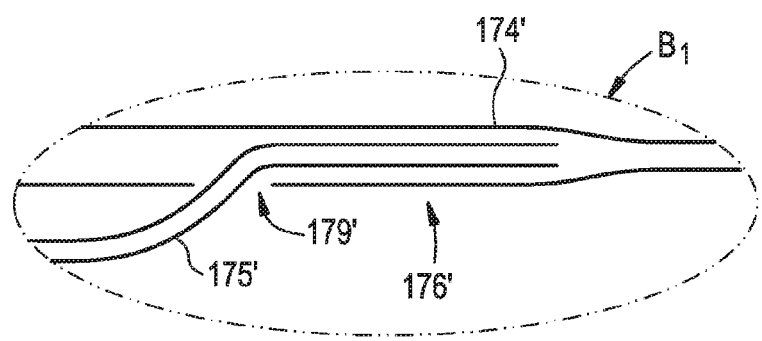

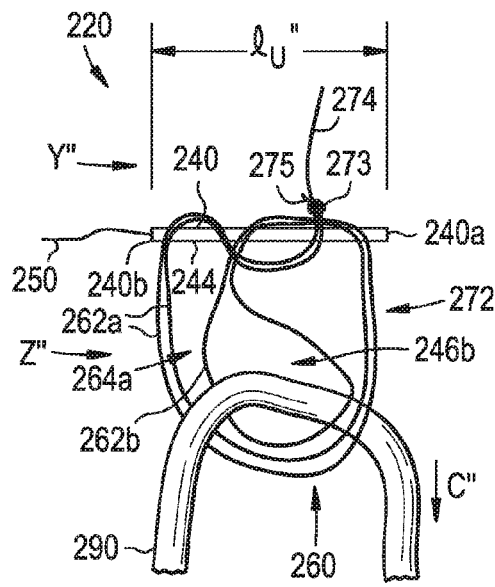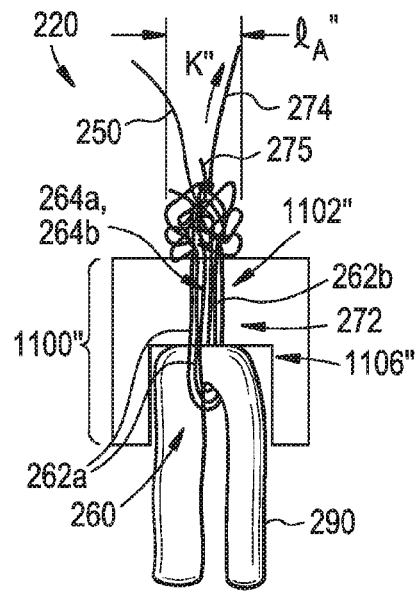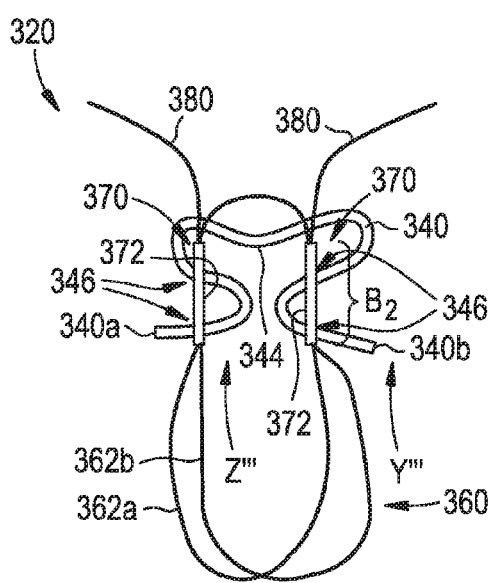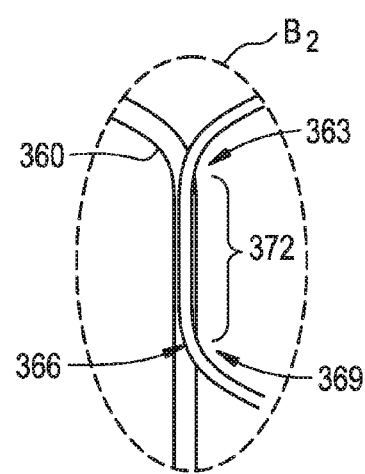

FLEXIBLE IMPLANT WITH ADJUSTABLE COILS

This application is a divisional of U.S. patent application Ser. No. 15/001,184, filed Jan. 19, 2016, and entitled "Flexible Implant with Adjustable Coils," which is hereby incorporated by reference in its entirety.

BACKGROUND

Field

The present disclosure relates to devices and methods for securing soft tissue to bone, and more particularly relates to using flexible implantable bodies in conjunction with a suture filament or repair construct formed to have adjustable coils for use in maintaining a location of a graft with respect to a bone.

Background

Joint injuries may commonly result in the complete or partial detachment of ligaments, tendons, and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves forming aligned femoral and tibial tunnels in a knee to repair a damaged anterior cruciate ligament ("ACL"). In one ACL repair procedure, a ligament graft is associated with a surgical implant and secured to the femur. A common ACL femoral fixation means includes an elongate, hard, metallic "button," sometimes referred to as a cortical button, having one or more filaments coupled to it. The one or more filaments can be formed into one or more coils or loops sized to receive the ligament graft(s) and allow an adequate length of the graft(s) to lie within the femoral tunnel while providing secure extra-cortical fixation. During procedures that use cortical buttons, the button is typically flipped after it passed through and out of the bone tunnel (e.g., a femoral tunnel) so that the button lies flat on a cortical surface while keeping the loop(s), and thus the graft(s) associated with the loop(s), in the tunnel. When flipping the button, however, the button can impinge on soft tissue disposed between the button and the bone, which can prevent the button from seating properly on the cortical surface and damage the impinged tissue. Further, it can be difficult to know when to "flip" the button. Current solutions to this problem are to measure a length of the bone tunnel and mark the filament associated with the button to indicate to the surgeon when the button is to be flipped, or providing a large enough opening to dispose a visualization device, like an endoscope or laparoscope, at the surgical site to see when the button exits the tunnel and can be flipped.

Another drawback to present devices and methods is that the bone tunnels through which an implant such as a cortical button, and the associated filament(s) and graft(s), pass can often be relatively large to accommodate the size of the implant and the graft(s) at various points during the procedure. A procedure for forming a bone tunnel, such as a femoral tunnel, through which the implant is passed and in which the graft(s) is disposed is illustrated in FIGS. 1A-1D. A bone 100 in which a tunnel 101 (FIG. 1D) is to be formed is illustrated in FIG. 1A. The procedure begins by using a Beath pin to form an initial guide tunnel 102 through an entire thickness of the bone 100, as shown in FIG. 1B, the tunnel 102 having a diameter approximately in the range of about 2 millimeters to about 2.5 millimeters. The Beath pin, which is typically thin and long, can remain disposed within the initial guide tunnel 102 to act as a guidewire to help position additional tools for drilling portions of the tunnel 101 having a larger diameter.

A reamer can be passed over the Beath pin to form a larger, passing tunnel 104 through an entire thickness of the bone 100, as shown in FIG. 1C. The previously formed initial guide tunnel 102 is illustrated in FIG. 1C using a dotted line to provide context of a diameter of the passing tunnel 104 as compared to a diameter of the initial guide tunnel 102. The diameter of the initial guide tunnel 102 is typically too small to have a typical cortical button passed through it, which is why the passing tunnel 104 is formed. A diameter of the passing tunnel 104 can be driven by the size of the width of the cortical button, and thus can be approximately in the range of about 4 millimeters to about 5 millimeters. A portion of the tunnel 101, as shown in FIG. 1D a distal portion 101$d$ that is formed into a graft tunnel 106, can then be further expanded and sized for having one or more grafts disposed in it. A reamer can be used to form the graft tunnel 106. The previously formed initial guide and passing tunnels 102, 104 are illustrated in FIG. 1D using dotted lines to provide context of a diameter of the graft tunnel 106 as compared to diameters of the initial guide and passing tunnels 102, 104. A diameter of the graft tunnel 106 can be based on the size of the graft(s) to be disposed therein, and can be approximately in the range of about 6 millimeters to about 8 millimeters.

Accordingly, it is desirable to have implantable bodies that are designed to sit more consistently and favorably with respect to the cortical surface and not impinge tissue disposed between the body and the bone. It is also desirable to have devices and methods that are designed to limit the number of steps used to form bone tunnels in which the implant(s) and graft(s) are disposed, avoids having to measure and mark components of the implant to assist in visualizing a location of the implant(s), and/or limits the amount of bone removed when forming bone tunnels into which the implants and grafts are passed and/or disposed.

SUMMARY

Devices and methods are generally provided for performing soft tissue (e.g., ACL) repairs. The devices and methods use flexible and/or soft bodies as the implant or body that ultimately rests against the cortical bone, in conjunction with filament formed into one or more loops or coils to maintain a location of a graft(s) with respect to the flexible and/or soft body, and thus the bone against which the body rests. The designs of the devices and methods provided for in the present disclosure allow for portions of the bone tunnels through which only the implant and not the graft(s) pass to be smaller when compared to existing techniques, and also reduce the possibility of the implant not sitting properly against the cortical bone and/or impinging tissue between the implant and the bone. Additionally, mechanisms for communicating to a surgeon that the flexible and/or soft body has passed through a bone tunnel and can be actuated to set the location of the implant with respect to the bone are also provided. As a result, many of the disclosures provided for herein make it so visualization techniques such as measuring bone tunnels and marking implants, filaments, and/or grafts are no longer necessary.

In one exemplary embodiment, a surgical implant includes a flexible filament body and a suture filament extending through the flexible filament body at two or more separate locations on the flexible filament body to form one or more coils. The configuration is such that a portion of each coil is disposed on a top side of the body and a portion of each coil is disposed on a bottom side of the body, with each coil defining an opening for that coil. The suture filament includes a slidable portion formed from the filament. Movement of the slidable portion toward and away from the flexible filament body causes a size of at least one opening of the one or more coils to change. A first and a second location at which the suture filament extends through the flexible filament body are located on opposed sides of the flexible filament body from each other along a length of the flexible filament body with the slidable portion of the suture filament being disposed therebetween. For example, the first location can be disposed on one side along a length of the body, the second location can be disposed on a second, opposed side along the length of the body, and the slidable portion of the suture filament can be disposed between the first and second locations, e.g., approximately at a midpoint along the length of the body. The flexible filament body and the suture filament are configured so application of tension to the one or more coils in a direction away from the flexible filament body causes the flexible filament body to constrict such that the first and second locations on the flexible filament body are located closer together than they were prior to the flexible filament body constricting when the flexible filament body is extended along its length.

A tensioning tail can extend from the slidable portion of the suture filament. The tail can be configured to move the slidable portion to change the size of the at least opening of the one or more coils. In some embodiments, the tensioning tail is formed from the suture filament. In such instances, the sliding portion can include a slidable knot that is slidably adjustable by applying tension to the tensioning tail. Further, the slidable knot can be a self-locking knot.

A distance extending between terminal, lengthwise ends of the flexible filament body as measured prior to being constricted can be greater than a distance extending between terminal, lengthwise ends of the flexible filament body as measured after the flexible filament body is constricted. The suture filament can include a hollow portion, and a sliding portion can include a portion of the suture filament disposed within the hollow portion. In such embodiments, the portion of the suture filament disposed within the hollow portion can be adjusted by applying tension to the tensioning tail. Further, the suture filament can also include a second hollow portion and a second sliding portion, with the second sliding portion including a portion of the suture filament disposed within the second hollow portion. In such embodiments, the portion of the suture filament disposed within the second hollow portion can be adjusted by applying tension to a second tensioning tail formed from the suture filament. The second tensioning tail can extend from the second sliding portion and can be configured to move the second sliding portion to change the size of at least one opening of the one or more coils.

In some embodiments, a pliable feedback unit can be disposed in a portion of the flexible filament body. Alternatively, a pliable feedback unit can be coupled to a terminal end of the flexible filament body. In either instance, the pliable feedback unit can be configured to produce an audible sound and/or tactile feedback when it moves from a bent configuration to a straight configuration. A feedback unit in some embodiments can have a known length extending from a terminal end of the flexible filament body, which can provide information about a location of the flexible filament body in view of the known length of the feedback unit. A feedback unit in some embodiments can be rigid and can be coupled to the flexible filament body by way of a connecting filament. The rigid feedback unit can be configured to engage bone surrounding a tunnel to prevent the suture filament from passing through the tunnel.

In another exemplary embodiment, a surgical implant includes a filament body, a suture filament extending through the filament body at two or more separate locations on the filament body to form one or more coils, and a tensioning tail. The filament body has an unstressed configuration, in which a first length of the filament body extends between opposed terminal ends of the filament body. A portion of each coil is disposed on a top side of the body and a portion of each coil is disposed on a bottom side of the body, with each coil defining an opening. The suture filament includes a slidable portion formed from the suture filament. Movement of the slidable portion towards and away from the filament body causes a size of at least one opening of the one or more coils to change. The tensioning tail extends from the slidable portion and is configured to move the slidable portion to change the size of the at least one opening of the one or more coils. Further, the filament body and the suture filament are configured such that the filament body is reconfigurable from the unstressed configuration to an anchoring configuration. More particularly, applying tension to the one or more coils in a direction away from the filament body causes the reconfiguration. In the anchoring configuration, the filament body has a second length that extends between opposed terminal ends of the reconfigured filament body. Both the first and second lengths are measured along a longitudinal axis of the filament body, and the first length is greater than the second length. In other words, the filament body is longer in the unstressed configuration than it is in the anchoring configuration when both lengths are measured along a longitudinal axis.

In some embodiments, the tensioning tail can be formed from the suture filament. In such embodiments, the slidable portion can include a slidable knot that is slidably adjustable by applying tension to the tensioning tail. Alternatively, in other such embodiments, the suture filament can include a hollow portion, and the slidable portion can include a portion of the suture filament being disposed within the hollow portion. In such embodiments, the portion of the suture filament disposed within the hollow portion can be adjusted by applying tension to the tensioning tail. Further, the suture filament can also include a second hollow portion and a second slidable portion, with the second slidable portion including a portion of the suture filament disposed within the second hollow portion. In such embodiments, the portion of the suture filament disposed within the second hollow portion can be adjusted by applying tension to a second tensioning tail formed from the suture filament. The second tensioning tail can extend from the second sliding portion and can be configured to move the second sliding portion to change the size of the opening of the one or more coils.

In some embodiments, a pliable feedback unit can be disposed in a portion of the filament body. Alternatively, a pliable feedback unit can be coupled to a terminal end of the filament body. In either instance, the pliable feedback unit can be configured to produce an audible sound and/or tactile feedback when it moves from a bent configuration to a straight configuration. A feedback unit in some embodiments can have a known length extending from a terminal end of the filament body, which can provide information about a location of the filament body in view of the known length of the feedback unit. A feedback unit in some embodiments can be rigid and can be coupled to the flexible filament body by way of a connecting filament. The rigid feedback unit can be configured to engage bone surrounding a tunnel to prevent the suture filament from passing through the tunnel.

One exemplary embodiment of a surgical method includes loading a graft onto one or more coils of a suture filament that is coupled to a flexible filament body having a shuttle filament extending from it. The shuttle filament is pulled through a bone tunnel, and thus the flexible filament body, the suture filament, and the graft are also pulled at least partially through the bone tunnel. The shuttle filament is pulled until the flexible filament body is pulled out of the tunnel and at least a portion of the suture filament and the graft remain in the tunnel. The flexible filament body is collapsed to draw terminal ends of the body that define a length of the body closer together, thereby placing the flexible filament body in an anchored configuration in which the flexible filament body is disposed on one side of the bone tunnel and the graft is disposed on an opposite side of the bone tunnel.

In some embodiments, collapsing the flexible filament body can include applying tension to the one or more coils in a direction away from the flexible filament body, which can cause the flexible filament body to collapse. The suture filament can include a slidable portion formed from the suture filament, and a tensioning tail can extend from the slidable portion. In such embodiments, the method can include applying tension to the tensioning tail to adjust a circumference of one or more coils of the suture filament. When the flexible filament body is pulled out of the tunnel, an audible sound and/or tactile feedback can be generated by a feedback unit associated with the flexible filament body to notify a user that the flexible filament body has passed through the tunnel. In some embodiments, the feedback unit can be disposed in a portion of the flexible filament body, while in some other embodiments, the feedback unit can be coupled to a terminal end of the flexible filament body.

BRIEF DESCRIPTION OF DRAWINGS

This invention will be more fully understood from the following detailed description taken in conjunction with the accompanying drawings, in which:

FIGS. 3A-3C are sequential, schematic, side, cross-sectional views of one exemplary method for using the surgical implant of FIG. 2 in conjunction with an ACL repair;

FIG. 7A is a schematic side view of another exemplary embodiment of a suture filament for use as part of a surgical implant;

FIG. 7B is a detail view of a coaxial region of the suture filament of FIG. 7A identified by arrow $B_1$;

FIG. 9A is a side view of the surgical implant of FIG. 8C in the initial, unactuated configuration and having a graft associated therewith;

FIG. 9B is a side view of the surgical implant of FIG. 9A associated with bone and in the actuated configuration;

FIG. 10A is a side view of yet another exemplary embodiment of a surgical implant;

FIG. 10B is a detailed, side, cross-sectional view of a portion of the surgical implant of FIG. 10A identified by arrow $B_2$;

DETAILED DESCRIPTION

Figure 1A:
FIGS. 1A-1D are sequential, schematic, side, cross-sectional views of a prior art method for forming a bone tunnel in a bone for use in conjunction with an ACL repair.
Figure 1B:
Figure 1C:
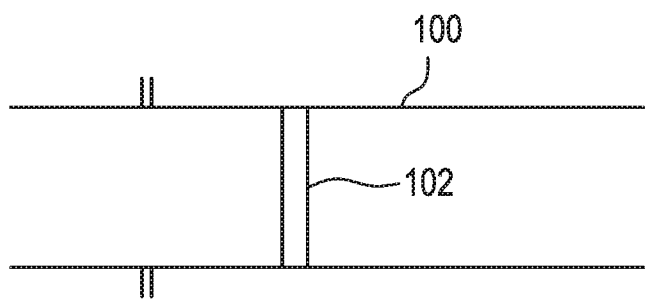
Figure 1D:
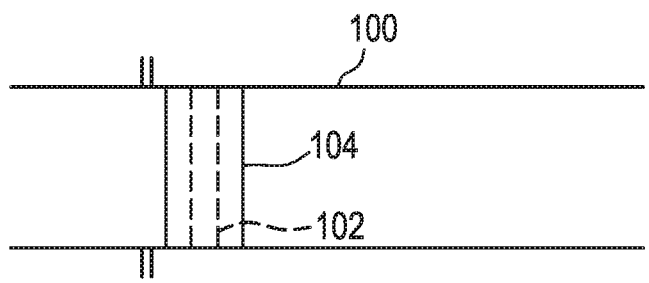

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Sizes and shapes of the devices, and the components thereof, can depend at least on the anatomy of the subject in which the devices will be used, the size and shape of components with which the devices will be used, and the methods and procedures in which the devices will be used.

In the present disclosure, like-numbered components of the embodiments generally have similar features and/or purposes. The figures provided herein are not necessarily to scale, although a person skilled in the art will recognize instances where they are to scale and/or what a typical size is when the drawings are not to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. To the extent features or steps are described herein as being a "first feature" or "first step," or a "second feature" or "second step," such numerical ordering is generally arbitrary, and thus such numbering can be interchangeable. Additionally, a number of terms may be used throughout the disclosure interchangeably but will be understood by a person skilled in the art. By way of non-limiting example, the terms "suture" and "filament" may be used interchangeably, and in some instances, simultaneously.

The present disclosure generally relates to a surgical implant for use in surgical procedures such as soft tissue (e.g., ACL) repairs. More particularly, the devices provided for herein use a flexible filament body in conjunction with one or more filaments associated with the body, the one or more filaments being configured to hold a graft(s) to be implanted at a surgical site. For example, the one or more filaments can be formed into one or more coils that can receive and hold a graft(s). In some embodiments, the coil(s) can be adjustable such that as a size of an opening(s) defined by a coil(s) is changed, the location of the graft(s) associated with the coil(s) with respect to the filament body can also change. The flexible filament body can be configured to be actuated between unstressed configurations in which terminal ends of the body are generally opposed to each other approximately along a longitudinal axis of the body, and an anchoring configuration in which the body becomes more compact while being able to be positioned proximate to a bone tunnel to secure a location of the graft associated with the flexible filament body within the bone tunnel. In some embodiments, a feedback unit can be incorporated with, coupled to, or otherwise associated with the filament body to help notify a surgeon where the filament body is with respect to a bone tunnel through which the body is passing.

Figure 2:
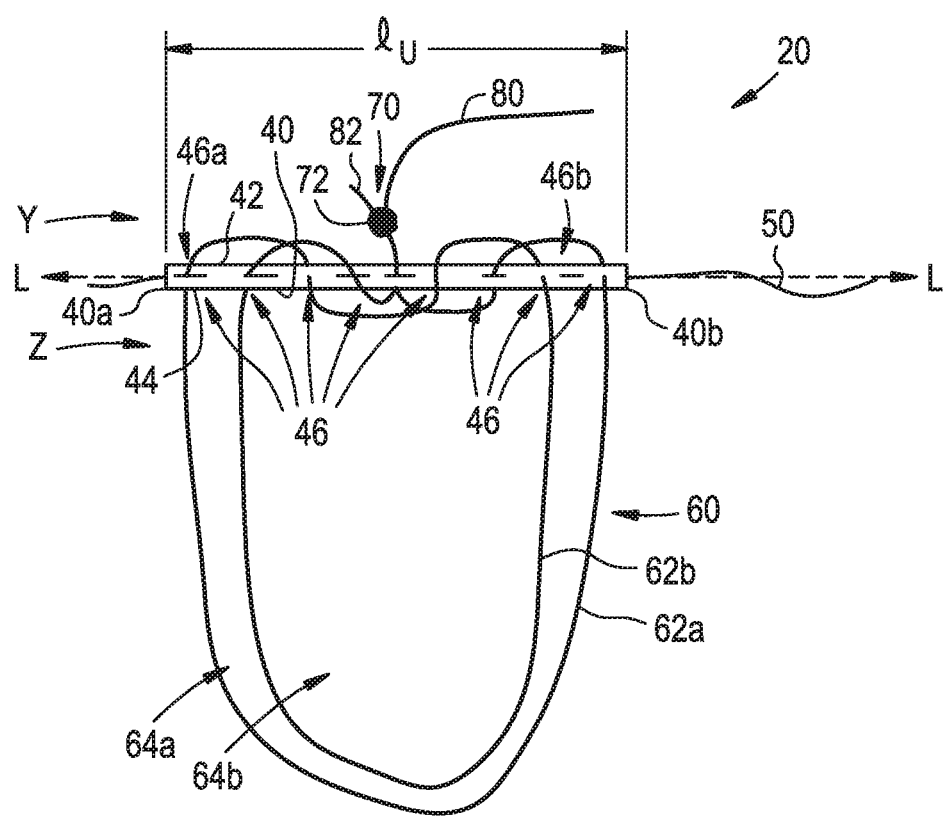
FIG. 2 is a side view of one exemplary embodiment of a surgical implant.

One exemplary embodiment of an implant 20 is provided in FIG. 2. As shown, the implant 20 includes a flexible filament body 40 and a suture filament 60, sometimes referred to as a suture repair construct, associated with the body 40. The flexible filament body 40 extends between terminal ends 40a, 40b to define a length $l_U$ of the filament, and thus the body 40. The body 40 can include a plurality of openings 46 that extend from a top side 42 to a bottom side 44 of the body 40. The openings 46 can be pre-formed by virtue of the construction and material of the filament (e.g., it can be a braided filament), or one or more of the openings 46 can be formed to receive suture filament, such as by creating openings where one did not previously exist or by expanding an existing opening to pass a repair construct through the formed opening.

As shown, the body 40 can have a leading tail 50 associated with it. In the illustrated embodiment, the leading tail 50 extends from the terminal end 40b and is part of the same material that is used to form the flexible filament body 40. In other embodiments, the leading tail 50 can extend from a different portion of the body 40 and/or it can be its own separate filament that is coupled to or otherwise associated with the body 40. The leading tail 50 can be used to help maneuver the flexible filament body 40 during a surgical procedure, such as passing it through a bone tunnel, as described in greater detail below.

The flexible filament body 40 is reconfigurable between an unactuated or unstressed configuration, shown in FIGS. 2 and 3A, and an actuated or anchoring configuration, shown in FIGS. 3B and 3C. In the unactuated or unstressed configuration, the terminal ends 40a, 40b approximately define the length $l_U$, although because the body 40 is flexible, the body 40 may not always be in an approximate straight line. This is illustrated by FIG. 3A, in which the flexible filament body 40 is still in the unactuated or unstressed configuration even though terminal end 40a is not co-linear with terminal end 40b along a longitudinal axis L of the body 40. Nevertheless, the length $l_U$ in the unactuated or unstressed configuration is the length of the filament when the body 40 is approximately in a straight line, as shown in FIG. 2.

In the actuated or anchoring configuration, the terminal ends 40a, 40b collapse towards a center 48 of the body 40 such that a resulting length $l_A$ of the body 40 is smaller than the length $l_U$. Notably, while the length $l_U$ is defined by the length when the body is approximately in a straight line, such a requirement is not applicable to the length $l_A$ because once the body is in the actuated or anchoring configuration, it is not easily manipulated back into a substantially collinear configuration along a longitudinal axis at least because it cannot be easily unwound. Further, in the illustrated embodiment of FIGS. 3B and 3C, the openings 46 of the body 40 through which the suture filament 60 is disposed also collapse towards the center 48, as demonstrated by the movement of openings 46a and 46b between FIGS. 3A and 3B. Thus, the terminal ends 40a, 40b, and as shown the openings 46 (e.g., 46a, 46b), are typically closer together in the anchoring configuration than they are in the unstressed configuration, However, again, in view of the flexible nature of the body 40, certainly the body 40 can be manipulated in other ways to place terminal ends 40a, 40b and/or openings 46 closer together even though the body 40 is in the unstressed configuration. Such movement does not depart from the spirit of the present disclosure. A person skilled in the art will recognize the differences between the unstressed and the anchoring configurations, and in particular how the lengths of the body 40 are defined in both configurations, and other ways the different configurations can be distinguished (e.g., density, distances between selection locations, etc.), in view of the present disclosures.

Another non-limiting example of a typically distinguishing characteristic between the two configurations is that generally a density of the body 40 is greater in the anchoring configuration than in the unstressed configuration. Even as the density of the body 40 increases, and a length defined by the terminal ends 40a, 40b decreases in the anchoring configuration as compared to the unstressed configuration, the length $l_A$ is still greater than a diameter $d_1$ of an adjacent bone tunnel 1102 so that the body 40 does not pass through the tunnel 1102, as described in greater detail below. As also described in greater detail below, actuating the flexible filament body 40 from the unstressed configuration to the anchoring configuration can be achieved by applying tension in a direction away from the flexible filament body 40, for instance by pulling approximately in a direction C on coils 62a, 62b of the suture filament 60, as shown in FIG. 3B. Typically pulling the leading tail 50 does not actuate the filament body 40, although in some other embodiments, a second tail can be associated with the filament body 40 with one tail being configured for the same purposes as the leading tail 50 as described herein, and the other tail being configured to actuate the flexible filament body 40. A person skilled in the art, in view of the present disclosures, would understand how to associate a second tail with the body 40 to allow the tail to initiate actuation of the body 40.

The suture filament 60 can be associated with the flexible filament body 40 in a number of different ways to allow the suture filament 60 to engage a graft 90 to be implanted and establish a location of the graft 90 with respect to the flexible filament body 40. As shown in FIGS. 2-3C, the suture filament 60 is passed through the openings 46 multiple times to form two coils or loops 62a, 62b for receiving a graft within openings 64a, 64b defined by the coils or loops 62a, 62b and the bottom side 44 of the flexible filament body 40. While a majority of the coils 62a, 62b are disposed below the flexible filament body 40, with an area below the flexible filament body 40 illustrated as area Z in FIG. 2, a portion is disposed above the flexible filament body 40, with an area above the flexible filament body 40 illustrated as area Y in FIG. 2. The suture filament 60 can also include a slidable portion 70 disposed above the flexible filament body 60. As shown, the slidable portion 70 is a sliding knot 72. A number of different sliding knots can be used, including but not limited to a Lark's Head knot, a Buntline Hitch knot, a Tennessee Slider knot, a Duncan Loop knot, and a Hangman's Noose knot. The knot 72 can also be self-locking.

One or more filament tails 80, 82 can extend from the slidable portion. In the illustrated embodiment, two tails or limbs 80, 82 formed by opposed terminal ends of the suture filament 60 extend from the knot 72, with one tail 80 serving as a closure or tensioning tail operable to adjust a size of the openings 64a, 64b of the coils 62a, 62b, and the other tail 82 serving as a stationary tail, on which one or more half-hitches can be formed at the conclusion of procedure to maintain a location of the knot 72 with respect to the flexible filament body 40. In other embodiments, both tails 80, 82 can be operable to adjust a size of one or more openings of the coils. The size of the openings 64a, 64b can be adjusted, for example, by applying tension away from the knot 72, as shown approximately in a direction K in FIG. 3C, thereby sliding the tensioning tail 80 in that direction and causing the size of the openings 64a, 64b to decrease.

The implant 20 can be used in conjunction with a bone tunnel 1100, e.g., a femoral tunnel. Some exemplary descriptions and illustrations of methods for forming bone tunnels are provided later herein with respect to FIGS. 21A-21C, and are thus not discussed in this section. FIGS. 3A-3C provide for method steps involved with implanting and, after passing a flexible filament body 40 of the implant 20 through the bone tunnel 1100, actuating the body 40 into the anchoring configuration. As shown in FIG. 3A, the bone tunnel 1100 includes the implant-receiving tunnel 1102 and a graft tunnel 1106, with the graft tunnel 1106 having a diameter $d_2$ that is greater than the diameter $d_1$ of the implant-passing tunnel 1102. As also shown in FIG. 3A, the implant 20 has a graft 90 disposed through both openings 64a, 64b, thus providing greater strength than if the graft 90 was passed through just one of the two openings. The graft 90 can be associated with the coils 62a, 62b at any time. After the filament body 40 is pulled through the tunnel 1100 by way of the leading tail 50, it is still in an unstressed configuration, with at least a portion of the coils 62a, 62b extending therefrom still disposed within at least a portion of the tunnel 1100.

Tension can be applied to the filament body 40 by applying tension to the graft 90 approximately in the direction C away from the body as shown in FIG. 3B. This causes the flexible filament body 40 to constrict and advance from the unstressed configuration to the actuated or anchoring configuration. As discussed above, the length $l_A$ of the filament body in the anchoring configuration, which as shown can also be considered a diameter of the resulting body 40, is greater than the diameter $d_1$ of the implant-passing tunnel 1102 that is adjacent to the body 40. Tension can then be applied to the closure tail 80 to decrease a size of the openings 64a, 64b, which in turn pulls the graft 90 towards and into the tunnel 1100, as shown in FIG. 3C. One or more half-hitches can be formed proximate to the sliding knot 72 to lock the sliding knot 72 in place, and thus maintain a location of the knot 72, the coils 62a, 62b, and the graft 90 with respect to the body 40.

Notably, although in the illustrated embodiment the flexible filament body 40 is actuated to move into the anchoring configuration by applying tension to the graft 90, and thus the coils 62a, 62b, a person skilled in the art, in view of the present disclosures, will recognize a variety of other components and methods that can be used to initiate the reconfiguration of the body 40 from the unstressed configuration to the anchoring configuration. By way of non-limiting example, in some embodiments, a separate actuation limb or tail can extend from the filament body 40, and can be used to initiate the collapse of the body 40. Such a tail can extend away from the body 40 from a similar location as the leading tail 50, can extend away from the body 40 from the opposite terminal end 40a, or from an intermediate portion of the body 40. Likewise, although in the illustrated embodiment two coils 62a, 62b are used to support a single graft 90, in other embodiments, each coil 62a, 62b can have a graft associated therewith, and the two tails 80 and 82 can be configured to individually control respective coils 62a, 62b such that the grafts can be selectively moved by applying tension to either of the two tails 80, 82. Exemplary disclosures related to forming coils from a suture filament, and using the same during a surgical procedure, are provided for at least in U.S. Patent Application Publication No. 20140257346 of Sengun, et al. and U.S. Patent Application Publication No. 20150157449 of Gustafson, et al., the content of each which is incorporated by reference herein in their respective entireties. A person skilled in the art would be able to incorporate those teachings that are incorporated by reference into the implants provided for herein, including using such teachings in conjunction with the flexible filament bodies, without much difficulty in view of the present disclosures.

Figure 4:
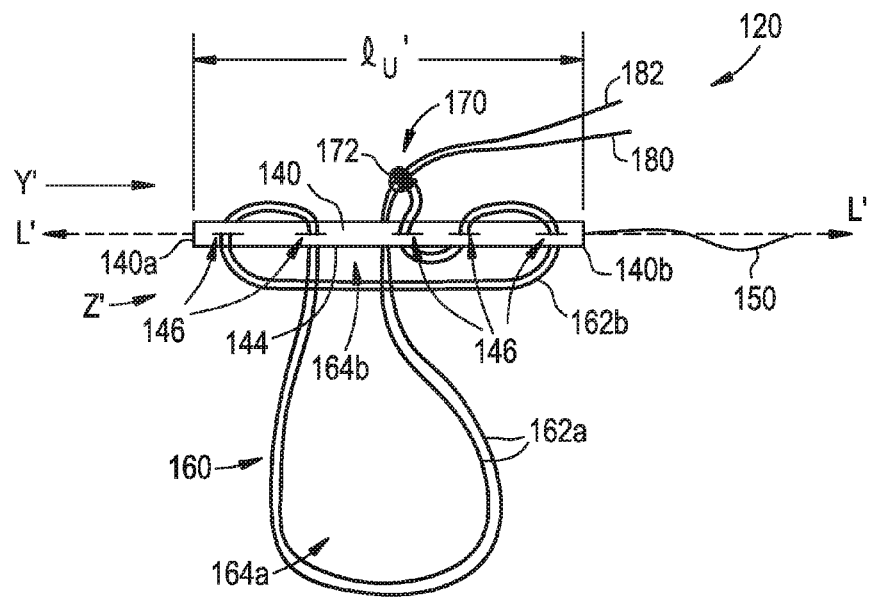
FIG. 4 is a side view of another exemplary embodiment of a surgical implant.

FIG. 4 provides an alternative embodiment of an implant 120 having a flexible filament body 140 and a suture filament or suture construct 160 associated with the body 140. The filament body 140 is similar to the filament body 140 of FIGS. 2-3C, and includes terminal ends 140a, 140b that define a length $l_U'$ as shown when the body 140 is in an unactuated or unstressed configuration and the terminal ends 140a, 140b are substantially co-linear along a longitudinal axis L' of the body 140 as shown. Multiple openings 146 exist in the body 140 for having the repair construct 160 passed therethrough, and a leading tail 150 extends from the terminal end 140b to help maneuver the flexible filament body 140 during a surgical procedure. The body 140 is reconfigurable between the unactuated or unstressed configuration illustrated in FIG. 4 and an actuated or anchoring configuration illustrated in FIGS. 5A and 5B, in which a length $l_A'$ of the body 140 is defined as approximately as a diameter of the resulting collapsed body 140.

The suture filament or repair construct 160 can be associated with the flexible filament body 140 in a number of different ways to allow the suture filament to engage a graft 190 to be implanted and establish a location of the graft 190 with respect to the filament body 140. As shown in FIGS. 4-5B, the suture filament 160 is passed through the openings 146 multiple times to form two coils or loops 162a, 162b, at least one of which can be used for receiving the graft 190 within the opening 164a, 164b defined by the respective coil or loop 162a, 162b and a bottom side 144 of the flexible filament body 140. The coils 162a, 162b are different than those of FIGS. 2-3C in that each coil includes two limbs of filament passing through each opening 146 of the filament body 140 rather than just one limb. While a majority of the coils 162a, 162b are disposed below the flexible filament body 140, with an area below the flexible filament body illustrated as area Z' in FIG. 4, a portion is disposed above the flexible filament body 140, with an area above the flexible filament body illustrated as area Y' in FIG. 4.

The suture filament 160 can also include a slidable portion 170 disposed above the flexible filament body 140. As shown, the slidable portion 170 is a sliding knot 172. A number of different sliding knots can be used, including but not limited to a Lark's Head knot, a Buntline Hitch knot, a Tennessee Slider knot, a Duncan Loop knot, and a Hangman's Noose knot. The knot 172 can also be self-locking. The construct 160 can also include one or more closure tails or limbs 180, 182 that extend from the slidable portion 170, and which can be operable to control a size of the openings 164a, 164b in manners described herein or otherwise known to those skilled in the art. In the illustrated embodiment, both tails 180, 182 serve as closure tails, and thus tension applied to either can change a size of at least one of the openings 164a, 164b. In other embodiments, one of the tails 180, 182 may be a stationary tail.

Figure 5A:
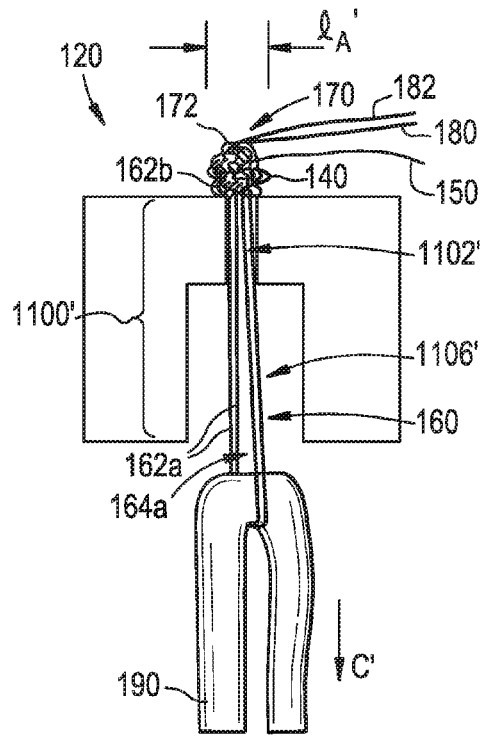
FIGS. 5A and 5B are sequential, schematic, side, cross-sectional views of one exemplary method for using the surgical implant of FIG. 4 in conjunction with an ACL repair.
Figure 5B:
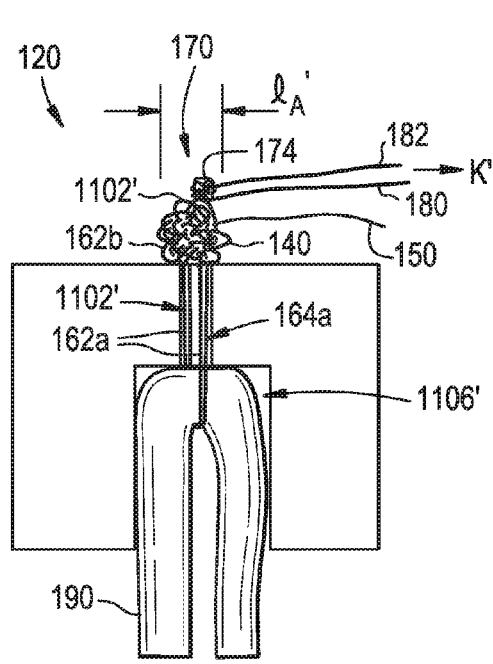

FIGS. 5A and 5B both illustrate the flexible filament body 140 in the actuated or anchoring configuration with a graft 190 passing through the openings 164a. The implant 120 is used in conjunction with a bone tunnel 1100', e.g., a femoral tunnel, having a configuration similar to the one described above, and thus includes an implant-receiving tunnel 1102' having a diameter that is less than a graft tunnel 1106'.

Similar to the flexible filament body 40, the flexible filament body 140 can be actuated by applying tension in a direction away from the body, such as by applying tension approximately in a direction C' to the graft 190 and/or the coil 162a, as shown in FIG. 5A. As shown in FIG. 4, the other coil 162b is proximate to the body 140 as the body 140 is actuated, and the coil 162b actually becomes part of the mass that defines the body 140 in the anchoring configuration, as shown in FIGS. 5A and 5B. Tension can then be applied to the closure tails 180, 182, for instance by applying it approximately in a direction K' as shown in FIG. 5B, to decrease a size of the opening 164a, and in turn pull the graft 190 towards and into the tunnel 1100' as shown in FIG. 5B. As also shown in FIG. 5B, one or more-half hitches 184 can be formed on at least one of the tails 180, 182 to lock the sliding portion 170 in place, and thus maintain a location of the sliding portion 170, the coil 162a, and the graft 190 with respect to the body 140.

Figure 6A:
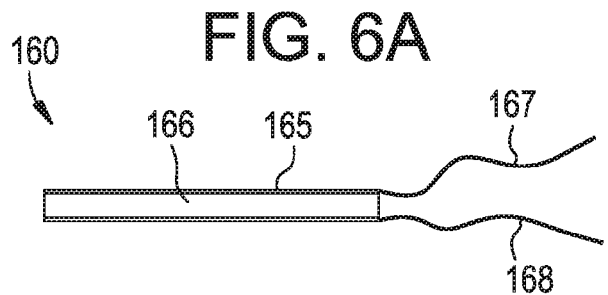
FIGS. 6A-6D are sequential, schematic, side views of one exemplary embodiment for forming a snare in a suture filament of the surgical implant of FIG. 4.
Figure 6B:
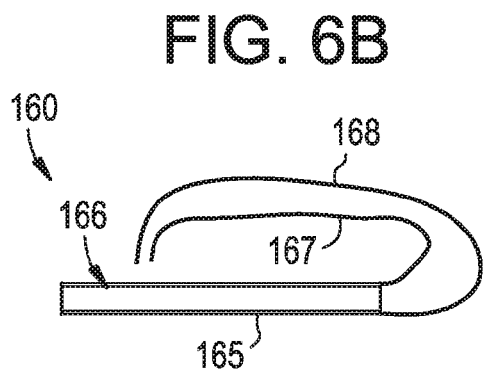
Figure 6C:
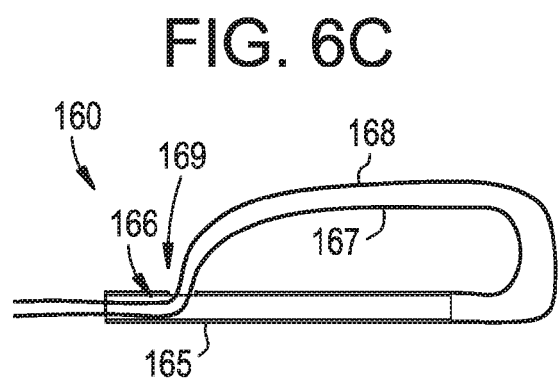
Figure 6D:
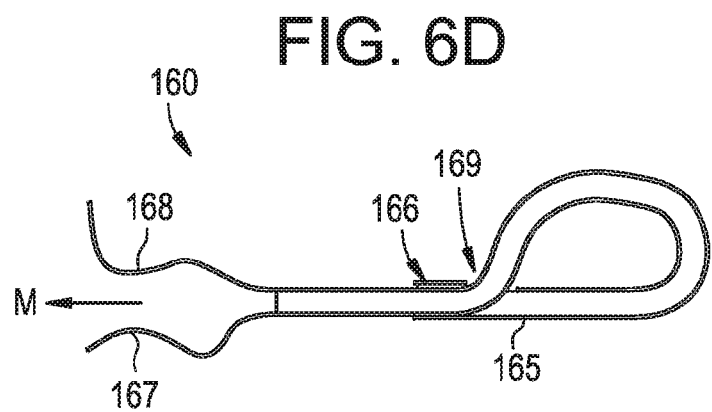

FIGS. 6A-6D illustrate one exemplary method for forming the repair construct 160 of FIGS. 4-5B. In this embodiment, the portion of filament 160 that forms the coils 162a, 162b is formed from a bifurcated suture filament having a tubular portion 165 with a core removed to form a cannulated portion 166 and first and second terminal limbs 167, 168. As shown in FIG. 6B, the terminal limbs 167, 168 can be curled back toward the tubular portion 165 to form a loop having an opening that defines the portions that will become the coils once associated with the filament body. As shown in FIG. 6C, a bore 169 can be formed on a side of the tubular portion 165 and the terminal limbs 167, 168 can be placed into the cannulated tubular portion 166 through the bore 169. Ends of the terminal limbs 167, 168 can be fed through the cannulated portion 166, and as shown in FIG. 6D, the terminal limbs 167, 168 can be pulled distally (approximately in a direction M in FIG. 6D) through the tubular portion 165 such that the tubular portion 165 is fed through itself. Accordingly, the filament that forms the coils can be collapsed by tensioning the limbs 167, 168 in approximately the direction M.

Although in the embodiment illustrated in FIGS. 6A-6D the portions of filament 160 that will become the coils are defined by a portion of a filament sliding inside of itself, a person skilled in the art will recognize that in alternative embodiments the filament 160 can be formed into a sliding knot to define the portion of filament that becomes the coils. A number of different sliding knots can be used, including but not limited to a Lark's Head knot, a Buntline Hitch knot, a Tennessee Slider knot, a Duncan Loop knot, and a Hangman's Noose knot, and the knot can be self-locking. To the extent the sliding knot used to form the portion of filament that becomes the coils impacts the operation of the coils, for instance whether a limb is pulled through a knot to change the position of the knot or a knot is slid along a limb to change the position of the knot, a person skilled in the art would be able to adapt these types of knots for use with the teachings of the present disclosure without departing from the spirit of the present disclosure.

FIGS. 7A and 7B illustrate an alternative embodiment of a repair construct 160' that can be used in conjunction with the implant 120 of FIGS. 4-5B. In this embodiment, a slidable portion is defined by a snare 172', which itself is defined by a sliding knot 173'. The portion that extends from an opposite side of the sliding knot 173', i.e., away from the snare 172', are limbs 174', 175' that form the portion of the construct 160' that will become the coils, and then, optionally, one of the two limbs is passed through itself in a coaxial region 176' so that a terminal end of the construct 160t' includes only a single filament 177'. More particularly, the repair construct 160' is generally formed from a single elongate filament that is folded to form a first limb 174' and a second limb 175'. The first limb 174' can generally be longer than the second limb 175', and the two limbs can be used to form both the snare 172' and the coaxial region 176'. The snare 172', which is disposed on a first end 160a' of the construct 160', can be configured to receive an opposite end 160b' of the construct 160' and is operable to collapse around a portion of the construct disposed in an opening 171' thereof. The portion that then extends through and out of the snare 172' defines the tail(s) used to adjust a size of openings of coils defined by the intermediate portions of filament 160'. The coaxial region 176' is generally configured to allow the shorter second limb 175' to be disposed within a volume of the first limb 174', thereby eliminating any additional component for suture management, such as a sleeve. The first limb 174' can then extend beyond the coaxial region 176' to form a tail 177' of the construct 160'.

The collapsible snare 172' can be formed using any number of techniques known to those skilled in the art. In the illustrated embodiment the first and second limbs 174', 175' are formed to include a sliding knot 173'. The sliding knot 173' is configured such that as it moves toward the coaxial region 176', a size of the opening 171' defined by the snare 172' increases, and as the knot 173' moves away from the coaxial region 176', the size of the opening 171' decreases. Some exemplary knot types include a Lark's Head knot, an Overhand Knot, and a Blood knot, and the knot can be a self-locking knot. A person skilled in the art will understand that in other configurations, a size of the opening 171' defined by the snare 172' may be adjusted in different manners, depending on the type of knot, desired use, etc. Some exemplary snare and formations thereof are described in U.S. Patent Application Publication No. 2012/0130424 of Sengun et al. and U.S. Pat. No. 9,060,763 to Sengun, the content of which is incorporated by reference in their entireties.

The coaxial region 176' in the illustrated embodiment is formed by passing terminal end 175t' of the second limb 175' into a volume of the first limb 174'. As shown in FIG. 7B, at least a portion of the first limb 174' can be cannulated, and an opening 179' on a side of the first limb 174' allows the second limb 175' to be disposed in the first limb 174'. The opening 179' can be created manually by forming a hole in the side of the first limb 174' and removing a core of the first limb 174' so that there is space to receive the second limb 175'. Alternatively, the filament of the first limb 174' can be a braided suture with a core removed from at least the portion of the first limb 174' that is part of the coaxial region 176', thereby allowing the first limb 174' to receive the second limb 175'. In other embodiments a core of a filament, braided or otherwise, is not removed and the second limb 175' is still disposed in first limb 174' using techniques known to those skilled in the art. A junction $B_1$ at which the second limb 175' engages the first limb 174' can be a self-maintaining junction. As a result, pulling on the tail 177' of the surgical construct 160' does not cause the second limb 175' to pull out of the first limb 174'. Rather, pulling on the tail 177' can actually force the first limb 174' to collapse around the second limb 175', thereby providing sufficient friction between the two limbs 174' and 175' to hold them together. The two limbs 174' and 175', however, can be separated manually at the junction $B_1$ by applying a sufficient amount of force. Although in the illustrated embodiment the junction $B_1$ is formed by inserting the terminal end 175t' of the second limb 175' into a portion of the first limb 174', a person skilled in the art will understand other ways by which the junction can be formed without departing from the spirit of the present disclosure.

The tail 177' of the construct 160' is formed by the remaining portion of the first limb 174' that extends beyond the coaxial region 176'. The tail 177' can be used, for example, to help lead insertion of the construct 160' into a flexible filament body, e.g., the bodies 40 and 140, among other things. Additionally, although in the illustrated embodiment a single filament is used to form the first and second limbs 174' and 175', a separate filament can be used for each of the first and second limbs 174' and 175' without departing from the spirit of the disclosures provided herein. Still further, a person skilled in the art will recognize that the methods of forming repair constructs described with respect to FIGS. 6A-7B are just some exemplary embodiments for suture filament or repair construct formations that can be used in conjunction with the disclosures to implants provided for herein. Many other methods can be used to form the repair constructs of the present disclosure without departing from the spirit of the present disclosure. By way of non-limiting example, in some embodiments the first and second limbs 174' and 175' can be maintained as separate limbs and used in a manner as illustrated with respect to the implant 120 of FIG. 4.

Figure 8A:
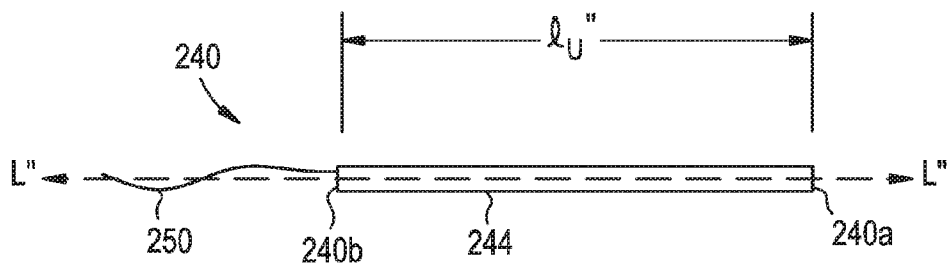
FIG. 8A is a side view of one exemplary embodiment of a filament body for use as part of an exemplary embodiment of a surgical implant.
Figure 8B:
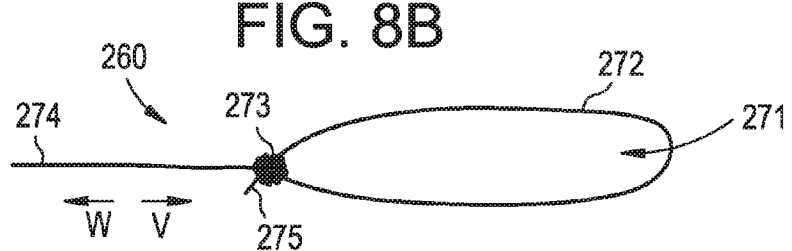
FIG. 8B is a side view of one exemplary embodiment of a suture filament for use as part of an exemplary embodiment of a surgical implant.
Figure 8C:
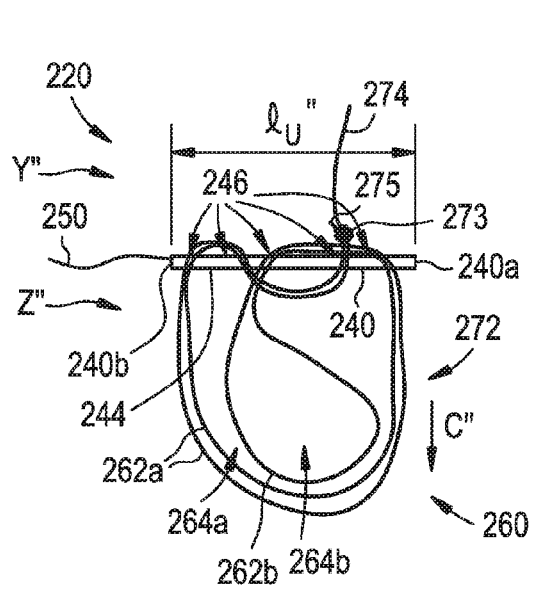
FIG. 8C is a side view of still another exemplary embodiment of a surgical implant, the implant including the suture filament of FIG. 8B passed through the filament body of FIG. 8A, and the implant being in an initial, unactuated configuration.
Figure 8D:
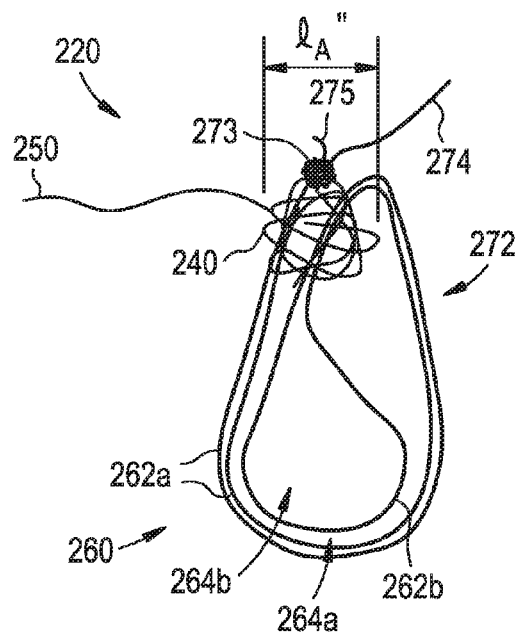
FIG. 8D is a side view of the surgical implant of FIG. 8C, the implant being in an actuated configuration.

Another exemplary embodiment of an implant 220 is provided for in FIGS. 8A-9B, with FIGS. 8A and 8B providing a flexible filament body 240 and a suture filament or repair construct 260, respectively, FIGS. 8C and 8D illustrating the body 240 and construct 260 coupled together or otherwise associated with each other in the unactuated or unstressed configuration (FIG. 8C) and the actuated or anchoring configuration (FIG. 8D) to form the implant 220, and FIGS. 9A and 9B illustrating the implant 220 associated with a graft 290 (FIGS. 9A and 9B) and implanted at a surgical site that includes a bone tunnel 1100", e.g., a femoral tunnel. As shown, the flexible filament body 240 of FIG. 8A is similar to the filament bodies of FIGS. 2-3C and 4-5B, and includes terminal ends 240a, 240b that define a length $l_U''$ as shown when the body 240 is in an unactuated or unstressed configuration and the terminal ends 240a, 240b are substantially co-linear along a longitudinal axis L" of the body 240. Multiple openings 246 (visible better in FIG. 8C based on locations through which the repair construct 260 passes) exist in the body 240 for having the repair construct 260 passed therethrough, and a leading tail 250 extends from the terminal end 240b to help maneuver the flexible filament body 240 during a surgical procedure. The body 240 is reconfigurable between the unactuated or unstressed configuration illustrated in FIG. 8C and an actuated or anchoring configuration illustrated in FIG. 8D, in which a length $l_A''$ of the body 240 is defined as approximately as a diameter of the resulting collapsed body 240.

The suture filament or repair construct 260 includes a snare 272, a sliding knot 273 that defines a size of the snare 272, and two tails 274, 275 extending from the snare 272. The portion of the filament 260 that is the snare 272 is the portion that will become the coils 262a, 262b (FIG. 8C) when the body 240 and suture filament 260 are coupled together. The sliding knot 273 can be configured such that as it moves approximately in a direction V as shown in FIG. 8B, a size of the opening 271 defined by the snare 272 decreases, and as the knot 273 moves approximately in a direction W as shown FIG. 8B, the size of the opening 271 increases. Some exemplary knot types include a Lark's Head knot, a Buntline Hitch knot, a Tennessee Slider knot, a Duncan Loop knot, and a Hangman's Noose knot, and the knot can be a self-locking knot. A person skilled in the art will understand that in other configurations, a size of the opening 271 defined by the snare 272 may be adjusted in different manners, depending on the type of knot, desired use, etc. Some exemplary snare and formations thereof are described in applications and patents previously incorporated by reference above.

As shown, one or more filament tails 274, 275 extend from the sliding knot 273. In the illustrated embodiment, two tails 274, 275 formed by opposed terminal ends of the suture filament 260 extend from the knot 273. One tail 274 serves as a closure tail operable to adjust a size of the opening 271 of the snare 272, and thus a size of openings 264a, 264b of the coils 262a, 262b (FIG. 8C) once the suture filament 260 is associated with the flexible filament body 240 as provided for with respect to FIGS. 8C and 8D, and the other tail 275 serves as a stationary tail, on which one or more half-hitches can be formed at the conclusion of procedure to maintain a location of the knot 273 with respect to the flexible filament body 240. At least in embodiments in which the sliding knot 273 is a locking knot, one or more half-hitches may not be used. As described above, in other embodiments, both tails 274, 275 can be operable to adjust a size of the snare 272, and thus a size of the openings 264a, 264b defined by the coils 262a, 262b.

The repair construct 260 can be associated with the flexible filament body in a number of different ways to allow the construct 260 to engage a graft to be implanted and establish a location of the graft with respect the flexible filament body 240. As shown in FIGS. 8C and 9A, the construct 260 is passed through the openings 246 multiple times to form two coils or loops 262a, 262b for receiving a graft 290 (FIGS. 9A and 9B) within openings 262a, 264b defined by the coils or loops 262a, 262b and a bottom side 244 of the flexible filament body 240. The implant 20 had a single limb of filament define each coil 62a, 62b for receiving a graft, while the implant 120 had two limbs of filament define each coil 162a, 162b for receiving a graft. The implant 220 includes one coil having each configuration. As shown in FIG. 8C, the first coil 262a includes two limbs, each defining the opening 264a for receiving a graft, while the second coil 262b includes a single limb that defines the opening 264b for receiving a graft. In use as illustrated in FIGS. 9A and 9B, the three limbs and two coils 262a, 262b are used together to provide additional strength for holding a single graft 290. A person skilled in the art, in view of the present disclosures, however, will recognize a variety of different ways coils can be formed and used separately and together to receiving one or more grafts. Further, in the illustrated embodiment, unlike previously illustrated embodiments, the slidable portion or knot 273 is not disposed centrally with respect to flexible filament body 240. The slidable portion of the repair constructs of any of the implants provided for herein can generally disposed anywhere along a length of the flexible filament body of the implants.

While a majority of the coils 262a, 262b are disposed below the flexible filament body 240, with an area below the flexible filament body 240 illustrated as area Z" in FIGS. 8C and 9A, a portion is disposed above the flexible filament body 240, with an area above the flexible filament body 240 illustrated as area Y" in FIGS. 8C and 9A. The slidable portion of the construct 260 that is disposed above the flexible filament body 240 is the sliding knot 273 that defines the snare 272. Similar to the earlier configurations, the filament body 240 can be actuated to form the anchoring configuration illustrated in FIGS. 8D and 9B by applying tension in a direction away from the body, such as by applying tension approximately in a direction C" away from the body 240 as shown in FIGS. 8C and 9A. Tension can then be applied to the closure tail 274, for instance by applying it approximately in a direction K" as shown in FIG. 9B, to decrease a size of the openings 264a, 264b, which in turn pulls the graft 290 disposed within the openings 264a, 264b towards the flexible filament body 240 and into the graft tunnel 1106". Similar to earlier embodiments, the bone tunnel 1100" illustrated in FIG. 9B includes both the graft tunnel 1106" and the implant-passing tunnel 1102", with a diameter $d_2''$ of the graft tunnel 1106" being larger than the diameter $d_1''$ of the implant-passing tunnel 1102". Formation of such tunnels 1102" and 1106" is provided for below with respect to FIGS. 21A-21C. One or more half-hitches can be formed on the tail 275 proximate to the sliding knot 273 to lock the sliding knot 273 in place, and thus maintain a location of the knot 273, the coils 262a, 262b, and the graft 290 with respect to the body 240.

FIGS. 10A-12C illustrate two exemplary embodiments of an implant 320, 320' that includes a flexible filament body 340, 340' and a suture filament or repair construct 360, 360' associated with the body 340, 340' in which a slidable portion 370, 370' of the construct 360, 360' is a coaxial region 372, 372'. In alternative embodiments, the coaxial region can be a separate sleeve disposed in locations illustrated where a hollow portion of the filament includes another portion of the filament passing therethrough.

Figure 12A:
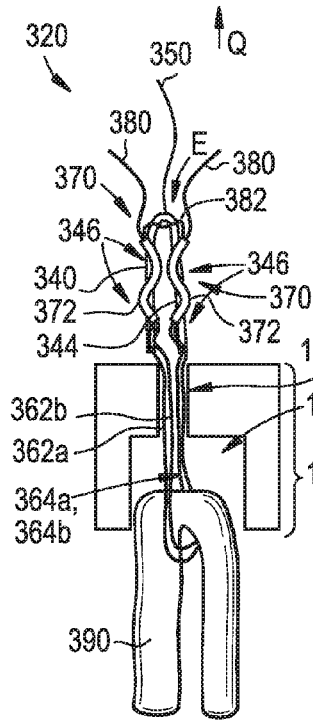
FIGS. 12A-12C are sequential, schematic, side, cross-sectional views of one exemplary method for using the surgical implant of FIG. 10A in conjunction with an ACL repair, the surgical implant differing from that of FIG. 10A in that it includes a filament tail.
Figure 12B:
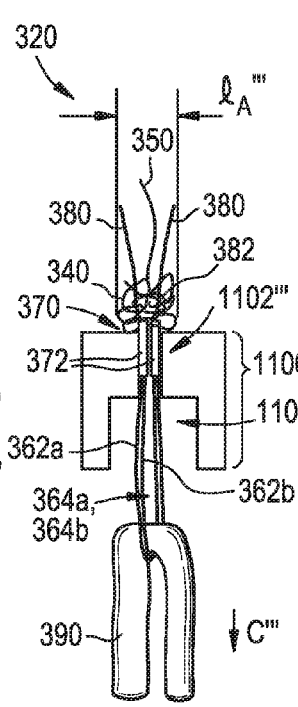
Figure 12C:
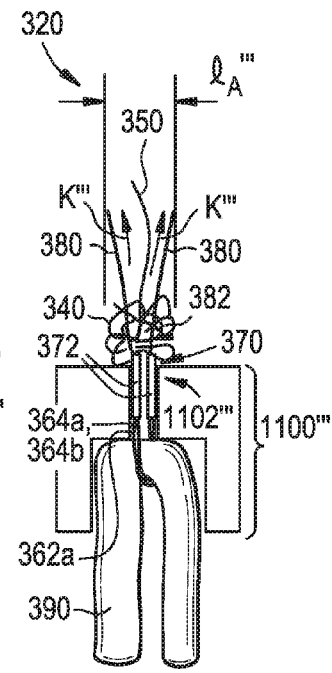

The implant 320 of FIG. 10A includes a flexible filament body 340 that is similar to the flexible filament bodies 40, 140, 240 described above except it does not include a leading tail. Alternatively, the body 340 can include a filament tail 350, as illustrated in FIGS. 12A-12C. The flexible filament body 340 includes terminal ends 340a, 340b that define a length $l_U'''$ (not shown) when the body 340 is in an unactuated or unstressed configuration and the terminal ends 340a, 340b are substantially co-linear along a longitudinal axis (not shown) of the body 340. Such a configuration is not illustrated, but is easily derivable based on other configurations and descriptions provided for herein and the knowledge of those skilled in the art. In embodiments in which a filament tail 350 is provided, the leading tail 350 can be disposed approximately at a midpoint E with respect to the length $l_U'''$ of the filament body 340, as shown in FIG. 12A. Alternatively, it can be disposed at other locations, including but not limited to a terminal end 340b as provided for in other embodiments herein. Similar to leading tails described above, in some embodiments the filament tail 350 can be a part of the filament that forms the flexible filament body 340, while in other embodiments the filament tail 350 can be a separate filament that is coupled to the flexible filament body 340 using any techniques known to those skilled in the art.

Multiple openings 346 exist in the body 340 for having the repair construct 360 passed therethrough, and similar to other embodiments, the body 340 is reconfigurable between an unactuated or unstressed configuration illustrated in FIGS. 10A and 12A, and an actuated or anchoring configuration illustrated in FIGS. 12B and 12C. Notably, in the illustrated unstressed configuration, the flexible filament body 340 can be bent, as provided for in FIGS. 10A and 12A, but it is still not in a denser, balled up type configuration like it is in the anchoring configuration as provided for in FIGS. 12B and 12C and in other embodiments of an implant herein. As described herein, however, the length $l_U'''$ of the flexible filament body 340 in the unstressed configuration is still a length that can be formed while the body 340 is unactuated, i.e., by the terminal ends 340a, 340b being collinear along a longitudinal axis of the body 340, while a length $l_A'''$ in an actuated or anchoring configuration is approximately the diameter of the balled up configuration, as illustrated in FIGS. 12B and 12C.

The coaxial region 372 that is the slidable portion 370 of the implant 320 can be formed in a variety of ways to form such regions known by those skilled in the art. In the illustrated embodiment, the filament 360 includes a hollow portion through which another portion of the filament passes. More specifically, as shown in FIG. 10B, a portion of the filament passed through a first opening 369 in the filament 360, through the hollow portion 366, and out of a second opening 363 in the filament. The portion of filament 360 disposed in the hollow portion 366 can change as a result of the slidable nature of the configuration, which in turn can adjust a size of openings of the coils or loops 362a, 362b formed by the filament 360, which as illustrated in FIG. 10A and described in greater detail below when describing how the filament 360 is coupled to or otherwise associated with the flexible filament body 340. The hollow portion 366 can be formed using any known techniques, including the filament 360 already being pre-formed to include a hollow portion or forming the hollow portion 366 by removing a portion of a core of the filament 360. The portion of the filament 360 that is disposed within the hollow portion 366 can engage with the portions of the filament 360 surrounding the openings 369, 363 through which it passes to act like a Chinese finger trap. Those skilled in the art will understand how such an interaction works, and thus a further explanation of a Chinese finger trap is unnecessary.

The repair construct 360 can be associated with the flexible filament body 340 in a number of different ways to allow the suture filament 360 to engage a graft to be implanted and establish a location of the graft with respect to the filament body 340. As shown in FIGS. 10A and 12A, the suture filament 360 is passed through the openings 346 multiple times to form two coils or loops 362a, 362b for receiving a graft 390 within openings 364a, 364b defined by the coils or loops 362a, 362b and a bottom side 344 of the flexible filament body 340. In the illustrated embodiment, the coaxial region 372 is part of the suture filament 360 that is passed through the flexible filament body 340, which can help keep a length of the implant 320 that goes through an implant-passing tunnel 1102''' (FIG. 12A) at a minimum (e.g., a diameter of the tunnel 1102''' being as small as 2 millimeters). Any portion of the suture filament 360 can be the portion that is passed through the flexible filament body 340.

As shown in FIGS. 10A and 12A, the coils or loops 362a, 362b are formed by portions of the suture filament 360 that extend away from the flexible filament body 340. More particularly, both a portion of the filament 360 that forms the hollow portion 366 of the coaxial region 372 through which another portion of the filament 360 passes, and the portion of the filament 360 that passes through the hollow portion 366 form the coils or loops 362a, 362b. Similar to other embodiments, while a majority of the coils 362a, 362b are disposed below the flexible filament body 340, with an area below the body illustrated as area Z''' in FIG. 10A, a portion is disposed above the body, with an area above the body illustrated as area Y''' in FIG. 10A.

More particularly, the coaxial regions 372 are disposed at either end of an intermediate portion 382 of the suture filament 360 disposed between the two coaxial regions 372. The first loop 362a is formed by the suture filament 360 extending away from the filament body and the coaxial region 372 that is proximate to the terminal end 340a of the filament body 340 in FIG. 10A, and then passing through the other coaxial region 372, i.e., the coaxial region 372 that is proximate to the terminal end 340b of the filament body 340 in FIG. 10A, with the portion that exits the other coaxial region 372 forming the closure limb 380. Likewise, the second loop 362b is formed by the suture filament 360 extending away from the filament body 340 and the other coaxial region 372, again the coaxial region 372 that is proximate to the terminal end 340b of the filament body 340 in FIG. 10A, and then passing through the first coaxial region 372, i.e., the coaxial region 372 that is proximate to the terminal end 340a of the filament body 340 in FIG. 10A, with the portion that exits the first coaxial region 372 forming the closure limb 380. Operation of the closure limbs 380 can be effective to adjust a size of all of the openings 364a, 364b of the coils or loops 362a, 362b.

Figure 11:
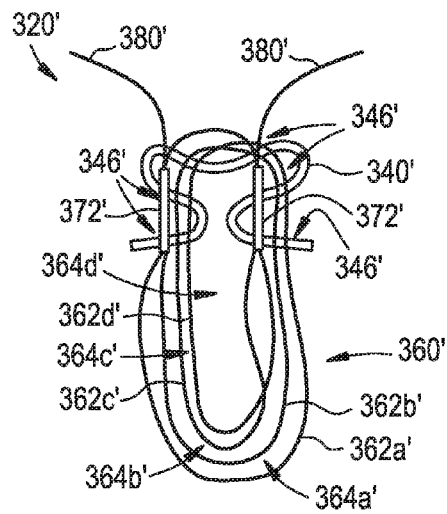
FIG. 11 is a side view of another exemplary embodiment of a surgical implant, the implant being similar to that of FIG. 10A except the implant of FIG. 11 includes four coils instead of two coils as provided for in the implant of FIG. 10A.

In alternative embodiments of an implant 320', more than two loops or coils can be formed. As shown in FIG. 11, four loops or coils 362a', 362b', 362c', 362d' are provided, with the two additional coils or loops being formed by passing suture filament 360' through openings 346' of a filament body 340' multiple more times. The multiple additional passes in the illustrated embodiment do not include additional coaxial regions 372', and instead involve the suture filament 360' just passing through the flexible filament body 340', although additional coaxial regions can be formed if desired. Similar to the earlier described embodiment, operation of closure limbs 380' can be effective to adjust a size of all of openings 364a', 364b', 364c', 364d' defined by the coils or loops 362a', 362b', 362c', 362d'.

FIGS. 12A-12C illustrate one exemplary method for passing the implant 320 through a bone tunnel 1100''', e.g., a femoral tunnel. The tunnel 1100'' includes both an implant-passing tunnel 1102''' and a graft tunnel 1106''', the formation of which is described below with respect to FIGS. 21A-21C. Additionally, a graft 390 is passed through the openings 364a, 364b formed by the coils 362a, 362b. The implant 320 can be passed through the tunnel 1100''' by applying tension to the filament tail 350 approximately in a direction Q to advance the implant 320 through the graft tunnel 1106''', and into and subsequently out of the implant-passing tunnel 1102'''. As shown, the flexible filament body 340 can also exit the implant-passing tunnel 1102''', while at least a portion of the coils 362a, 362b remains disposed within both the implant-passing and graft tunnels 1102''', 1106'''. As described earlier with respect to the leading tails 50, 150, 250, typically applying tension to the filament tail 350 does not cause the flexible filament body 340 to actuate. The flexible filament body 340 can be actuated, however, by applying tension to the one or more coils 362a, 362b in a direction away from the flexible filament body, as shown approximately in a direction C''' in FIG. 12B. The flexible filament body 340 then further collapses upon itself into a balled up, denser configuration as shown. In some embodiments, at least a portion of the coaxial region 372 can be drawn into the mass that forms the flexible filament body 340 in its anchoring configuration. As shown in FIG. 12C, tension can be applied to the closure limbs 380, for instance approximately in a direction K''', to decrease a size of the openings 364a, 364b of the coils 362a, 362b, and thus draw the graft 390 into, or further into, the graft tunnel 1106'''.

Both the flexible filament body 40, 140, 240, 340, 340' and the suture filament or repair construct 60, 160, 260, 360, 360' can be formed from a variety of materials in a variety of forms. The type of filaments and materials of the filaments for the body and the construct can be similar or different for the same implant. Typically, the materials that are used to form both the body and repair construct are what a person skilled in the art would consider to be soft materials, which helps minimize unwanted trauma on the tissue with which the implant is used. In one exemplary embodiment, the flexible filament body is formed using a surgical filament, such as a braided filament. The type, size, and strength of the materials used to form the flexible filament body can depend, at least in part, on the materials and configuration of the repair construct, the type of bone or tissue with which it will be used, and the type of procedure with which it will be used. In one exemplary embodiment the flexible filament body is formed from a #2 filament (about 23 gauge to about 24 gauge), such as an Orthocord™ filament that is commercially available from DePuy Mitek, Inc. or an Ethibond™ filament that is commercially available from Ethicon, Inc., Route 22 West, Somerville, N.J. 08876. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed.

The type, size, and strength of the materials used to form the suture filament or repair construct can likewise depend, at least in part, on the materials and configuration of the flexible filament body, the type of bone or tissue with which it will be used, and the type of procedure with which it will be used. In one exemplary embodiment the flexible material is a #2 filament (about 23 gauge to about 24 gauge), such as an Orthocord™ filament that is commercially available from DePuy Mitek, Inc or Ethibond™ filament available from Ethicon, Inc. Generally the filament is relatively thin to minimize any trauma to tissue through which it passes. In some embodiments the filament can have a size between about a #5 filament (about 20 gauge to about 21 gauge) and about a #5-0 filament (about 35 gauge to about 38 gauge). The Orthocord™ #2 filament can be useful because it has a braided configuration, which allows other components, including the filament itself, to pass through subcomponents of the braid without causing damage to the filament. Filaments configured to allow for a cannulated configuration, such as by removing a core therefrom or having a preformed cannulated configuration, can also be used. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filament bodies and the repair constructs of the present disclosure is primarily a matter of surgeon preference for the particular surgical procedure to be performed.

In addition to providing implants that can be less traumatic to tissue, and reduces an amount of bone removed to form a bone tunnel, the present disclosures also provide for embodiments that make it easier for a surgeon to identify a location of an implant during a surgical procedure. These embodiments come in a variety of forms, and one such embodiment is illustrated in FIGS. 13-14D.

Figure 13:
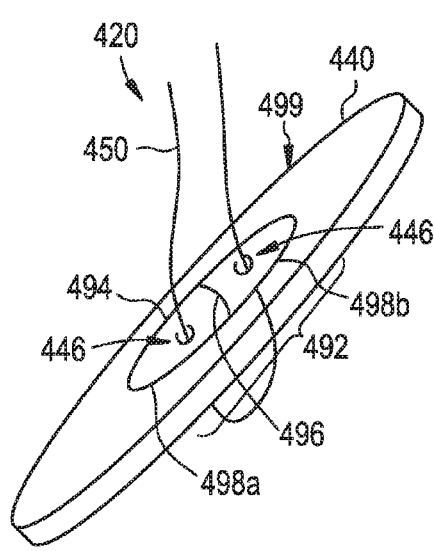
FIG. 13 is a perspective view of one exemplary embodiment of a surgical implant having one exemplary embodiment of a pliable feedback unit disposed approximately in a central portion of the implant.

As shown in FIG. 13, a feedback unit 492 is provided to assist a surgeon in knowing a location of an implant 420. The feedback unit 492 is a pliable body 494, sometimes referred to as a pledget, that includes a midpline 496 disposed approximately at a midpoint along its length l. In other embodiments, the midline 496 can be a hinge. Opposed plates 498a, 498b of the body 494 can rotate about the midline 496 between a straight and a bent configuration. More particularly, the plates 498a, 498b pledget 494 can be biased towards the straight configuration, but they can be configured to move to the bent configuration by applying sufficient pressure to the pledget 494, for instance by applying pressure to ends of the pledget 494 when it passes through a small space. The pledget 494 can be disposed within a flexible filament body, as shown, or in other embodiments it can be attached to an outer surface of the body 440 of the implant 420. In some embodiments, a filament tail 450 can be passed through openings 446 of the flexible filament body 440 and openings 499 formed through both plates 498a, 498b of the pledget 494, to be used to direct positioning of the flexible body 440, and thus the pledget 494, during a surgical procedure.

Figure 14A:
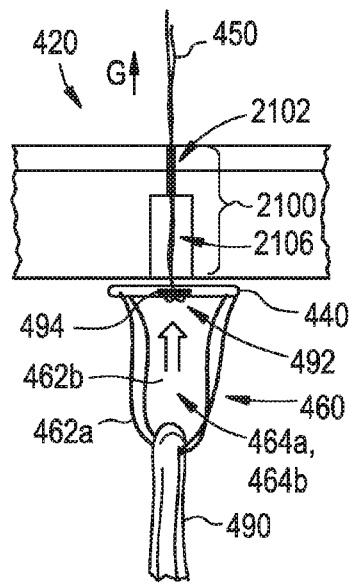
FIGS. 14A-14D are sequential, schematic, side, cross-sectional views of one exemplary embodiment for using the surgical implant of FIG. 13 in conjunction with an ACL repair.
Figure 14B:
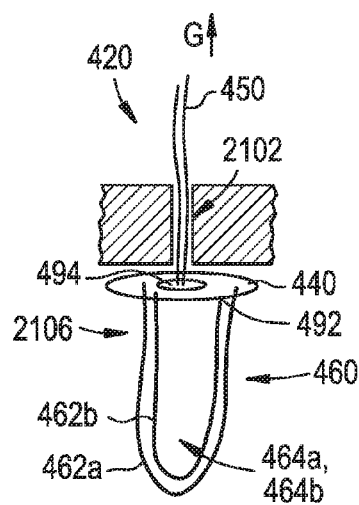
Figure 14C:
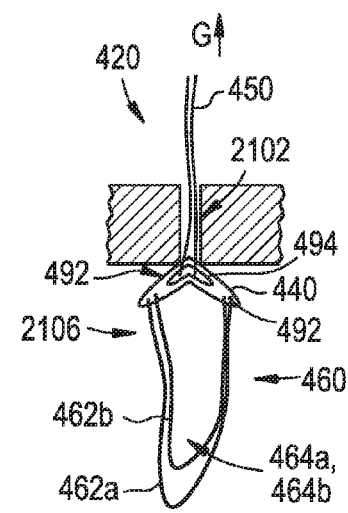
Figure 14D:
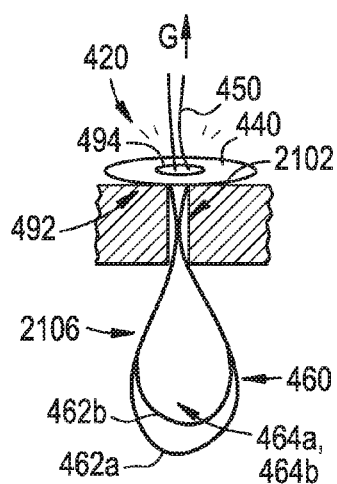

In use, the flexible filament body 440 can have a suture filament or repair construct 460 formed into coils 462a, 462b associated therewith to form the implant 420, with a graft 490 (only shown in FIG. 14A) disposed within openings 464a, 464b of the coils, and thus associated with the body 440, as shown in FIG. 14A. The implant 420 can be drawn through a bone tunnel 2100, e.g., a femoral tunnel, as shown the tunnel 2100 having both an implant-passing tunnel 2102 and a graft tunnel 2106, by applying tension to the filament tail 450 approximately in a direction G. The tunnel 2100 and pledget 494 can be sized such that as the flexible body 440 is passed through the graft tunnel 2106, the pledget 494 remains in the straight configuration, illustrated in FIGS. 14A and 14B, and when the body 440 passes into the implant-passing tunnel 2102, the pledget 494 moves into its bent configuration, as shown in FIG. 14C. When the pledget 494 exits the implant-passing tunnel 2102, it returns back to the straight configuration in view of the bias of the pledget 494, as shown in FIG. 14D. As the pledget 494 returns to the straight configuration, it can make an audible sound, thereby notifying a surgeon of the configuration change. When a surgeon hears this sound, the surgeon knows that the flexible filament body 440 has passed through implant-passing tunnel 2102, and thus the flexible filament body 440 can be actuated into the anchoring configuration as desired. In some instances, a surgeon may also feel the pledget 494 return to the straight configuration, for instance in the form of a tactile "click," thus providing an alternative notification that the flexible filament body 440 has passed through the implant-passing tunnel 2102, referred to herein as tactile feedback.

Figure 15A:
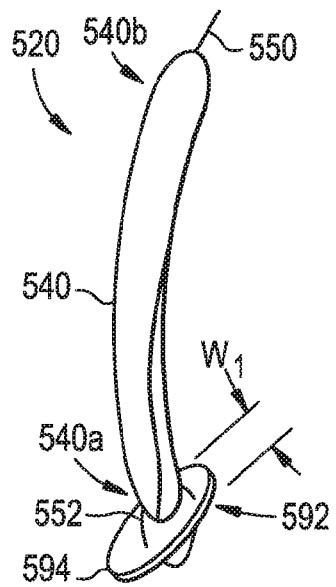
FIG. 15A is a side view of one exemplary embodiment of a surgical implant having one exemplary embodiment of a feedback unit disposed approximately at an end of the implant.
Figure 15B:
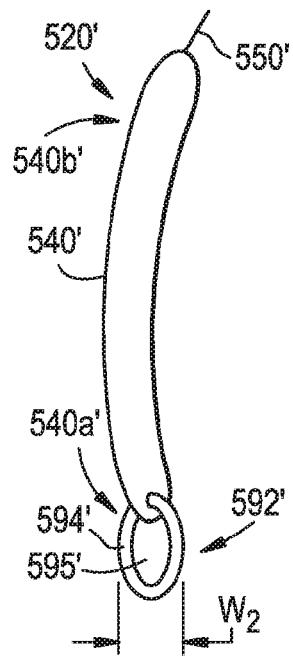
FIG. 15B is a side view of another exemplary embodiment of a surgical implant having another exemplary embodiment of a feedback unit disposed approximately at an end of the implant.
Figure 15C:
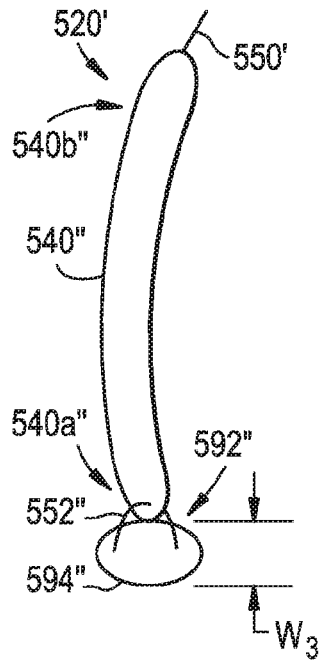
FIG. 15C is a side view of still another exemplary embodiment of a surgical implant having still another exemplary embodiment of a feedback unit disposed approximately at an end of the implant.
Figure 15D:
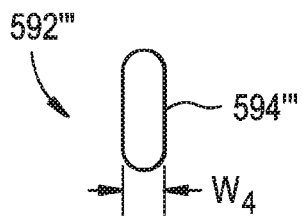
FIG. 15D is a top view of another exemplary embodiment of a feedback unit configured to be disposed approximately at an end of a surgical implant.
Figure 15E:
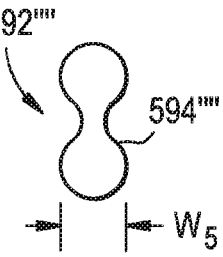
FIG. 15E is a top view of yet another exemplary embodiment of a feedback unit configured to be disposed approximately at an end of a surgical implant.

FIGS. 15A-16E provide for alternative feedback units 592, 592', 592'', 592''', 592'''' for use with implants 520, 520', 520'' (implants 520''', 520'''' for use with the feedback units of FIGS. 15D and 15E are not illustrated). The feedback units 592, 592', 592'', 592''', 592'''' in these figures are bodies or pledgets 594, 594', 594'', 594''', 594'''' designed to be disposed at a terminal end of a flexible filament body 540, 540', 540'' (flexible filament bodies 540''', 540'''' for use with the feedback units 592'', 592'''' of FIGS. 15D and 15E are not illustrated). Such a configuration can be helpful for configurations of flexible filament bodies 540, 540', 540'' having leading tails 550, 550', 550'' disposed at terminal ends 540b, 540b', 540b''. The bodies 594, 594', 594'', 594''', 594'''' can be pliable such that in a resting configuration a greatest width $w_1$, $w_2$, $w_3$, $w_4$, $w_5$ thereof is larger than a diameter of an implant-passing tunnel, but the bodies 594, 594', 594'', 594''', 594'''' can be compressed to pass through such a tunnel when tension is applied to the bodies, thus placing the bodies into a compressing configuration. The bodies 594, 594', 594'', 594''', 594'''' can have any number of shapes, five of which are illustrated in FIGS. 15A-15E. In the embodiments of FIGS. 15A-15C, the feedback unit 594, 594', 594'' is disposed at a distal, terminal end 540a, 540a', 540a'' of the flexible filament body 540, 540', 540'', while the embodiments of FIGS. 15D and 15E are also configured to be disposed at a distal, terminal end of a flexible filament body, although the feedback units 594''', 594'''' are illustrated by themselves in the figures.

The body 594 in FIG. 15A is shaped like an elliptical shim, the body 594' in FIG. 15B is shaped like a hoop that includes an opening 595', the body 594'' in FIG. 15C is shaped like a circular disk or puck, the body 594''' in FIG. 15D is shaped like an elliptical button, and the body 594'''' in FIG. 15E is shaped like an hourglass. The bodies 594, 594', 594'', 594''', 594'''' can be attached to the flexible filament bodies 540, 540', 540'' (flexible filament bodies 540''', 540'''' for use with the feedback units 592'', 592'''' of FIGS. 15D and 15E are not illustrated) using any techniques known to those skilled in the art. By way of non-limiting examples, a connecting filament 552, 552'' connects the bodies 594, 594'' to the flexible filament bodies 540, 540'' in FIGS. 15A and 15C, and the body 594' is passed through the flexible filament body 540' in FIG. 15B. The bodies 594, 594', 594'', 594''', 594'''' are generally kept adjacent to the terminal end 540b, 540b', 540b'' (terminal ends 540b''', 540b'''' for use with the feedback units 592'', 592'''' of FIGS. 15D and 15E are not illustrated) to provide for accurate notification that the flexible filament body has passed through a bone tunnel, as described below. Similar to the pledget 494, the notification or feedback provided by the bodies 594, 594', 594'', 594''', 594'''' can be audible and/or tactile.

FIGS. 16A-16E illustrate the implant 520 being used in an implant procedure in which the implant 520 is passed through a bone tunnel 2100', e.g., a femoral tunnel, the tunnel 2100' including an implant-passing tunnel 2102' and a graft tunnel 2106'. As shown, the implant 520 that includes the flexible filament body 540 and body 594 of the feedback unit 592, also includes a suture filament or repair construct 560 and a graft 590 passed through openings 564a, 564b formed by coils or loops 562a, 562b of the repair construct 560. The flexible filament body 540 includes the leading tail 550, and the repair construct 560 includes a slidable portion 570 disposed on a first side 542 of the body 540 having closure or tensioning limbs 580, 582 extending therefrom. A majority of a portion of the coils 562a, 562b are disposed on a second side 544 of the body 540.

Figure 16A:
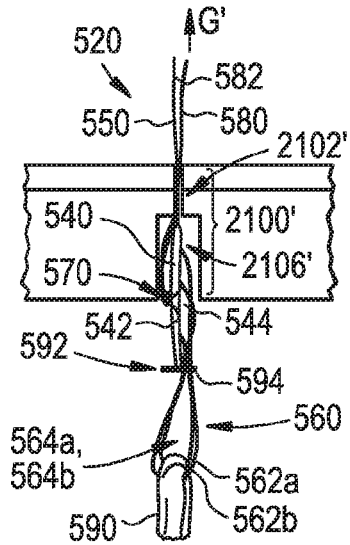
FIGS. 16A-16E are sequential, schematic, side, cross-sectional views of one exemplary embodiment for using the surgical implant of FIG. 15A in conjunction with an ACL repair.
Figure 16B:
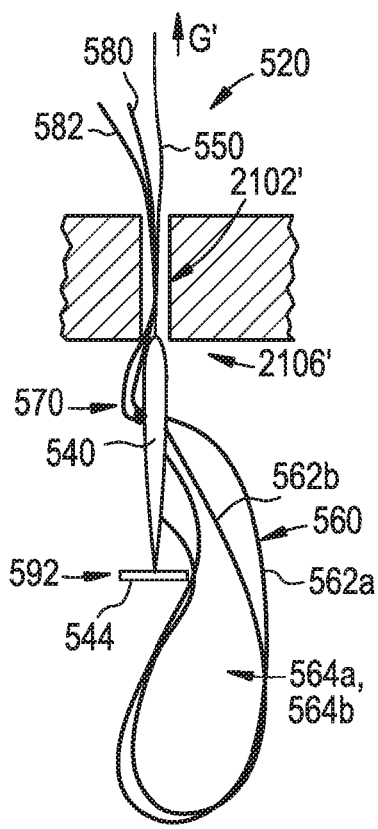
Figure 16C:
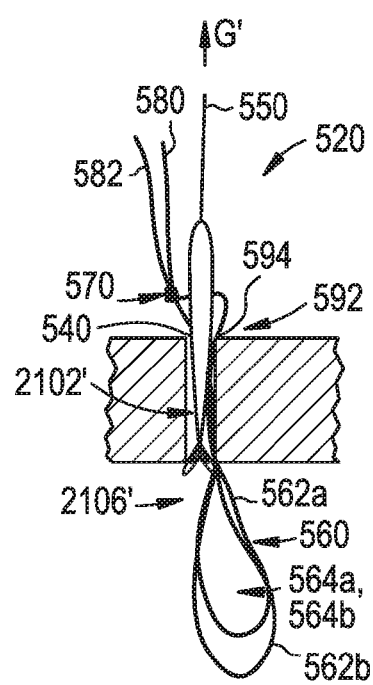
Figure 16D:
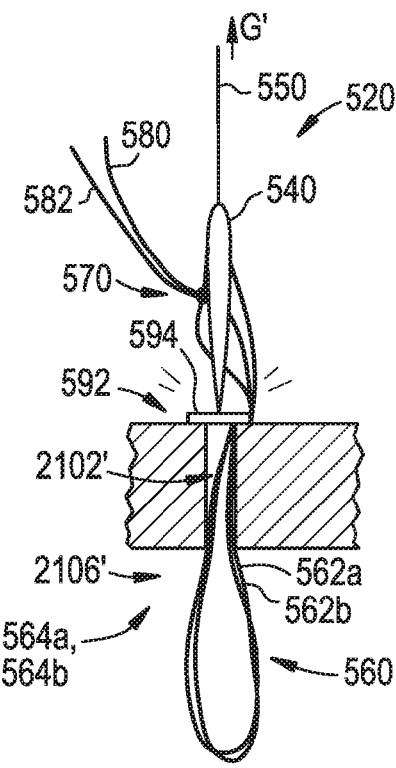
Figure 16E:
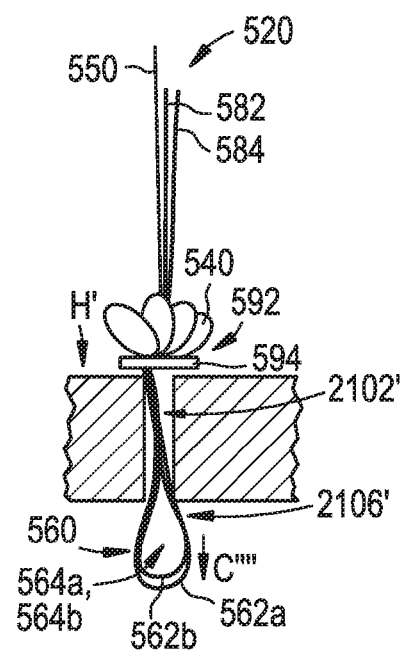

The implant 520 can be drawn into the graft tunnel 2106' and the implant-passing tunnel 2102' by applying tension to the leading end approximately in a direction G' as illustrated in FIG. 16A. The tunnels 2102', 2106' and body 594 can be sized such that as the body 594 is passed through the graft tunnel 2106', the body 594 remains in the resting configuration, illustrated in FIGS. 16A and 16B, and when it passes into the implant-passing tunnel 2102', it moves into its compressing configuration, as shown in FIG. 16C. When the body 594 exits the implant-passing tunnel 2102', it returns back to the resting configuration, a shown in FIG. 16D. As the body 594 returns to the resting configuration, it can make an audible sound, thereby notifying a surgeon of the configuration change. When a surgeon hears this sound, the surgeon knows that the flexible filament body 540 has passed through implant-passing tunnel 2102', and thus the flexible filament body 540 can be actuated into the anchoring configuration as desired, illustrated in FIG. 16E. Actuation of the flexible filament body 540 can be initiated using any of the techniques described herein, including by applying tension to the coils 562a, 562b in a direction away from the body 540, as shown by applying tension approximately in a direction C''''.

In this embodiment, the feedback unit 592 ends being disposed between the bone and the flexible filament body 540. As the flexible filament body 540 is actuated, it can apply a force on the body 594 of the feedback unit 592 approximately in a direction H' to help maintain the body 540 at a location adjacent to the bone tunnel, and thus the suture filament 560 within the bone tunnels 2102', 2106'. Further, or additionally, a surgeon may also feel the body 594 return to the resting configuration, thus providing an alternative notification that the flexible filament body 540 has passed through the implant-passing tunnel 2102'.

Figure 17:
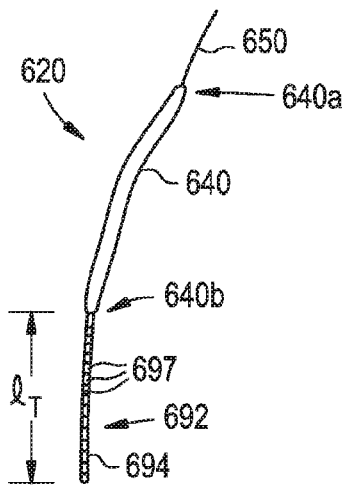
FIG. 17 is a side view of another exemplary embodiment of a surgical implant having another exemplary embodiment of a feedback unit disposed approximately at an end of the implant.
Figure 18A:
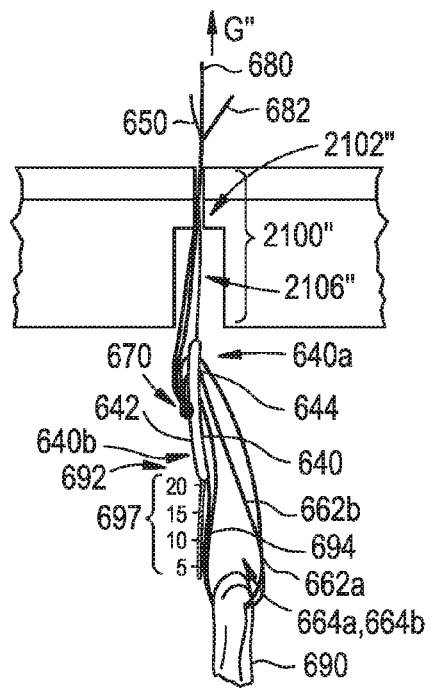
FIGS. 18A-18E are sequential, schematic, side, cross-sectional views of one exemplary embodiment for using the surgical implant of FIG. 17 in conjunction with an ACL repair.
Figure 18B:
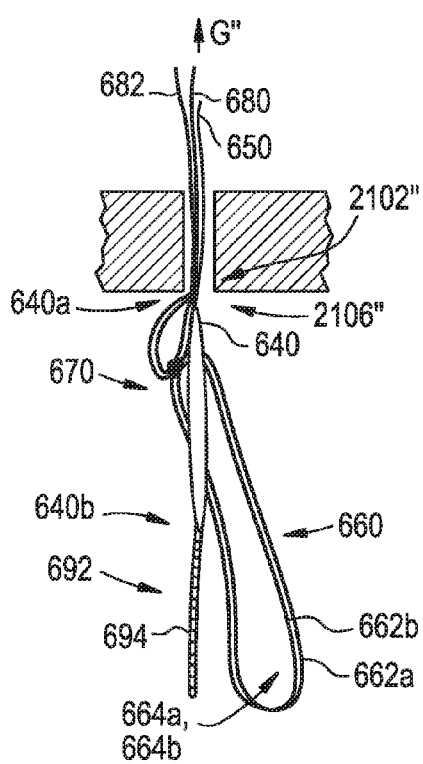
Figure 18C:
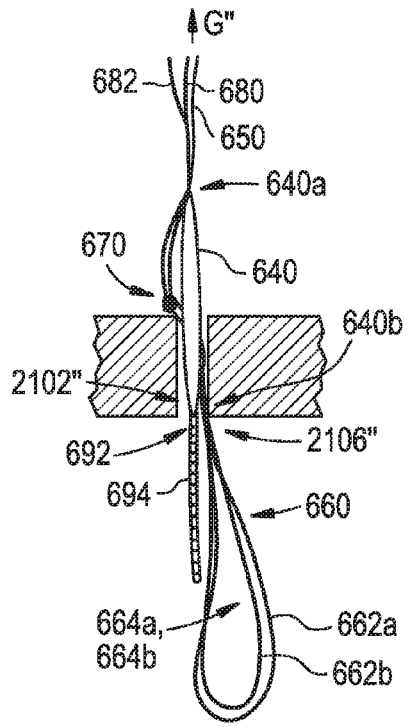
Figure 18D:
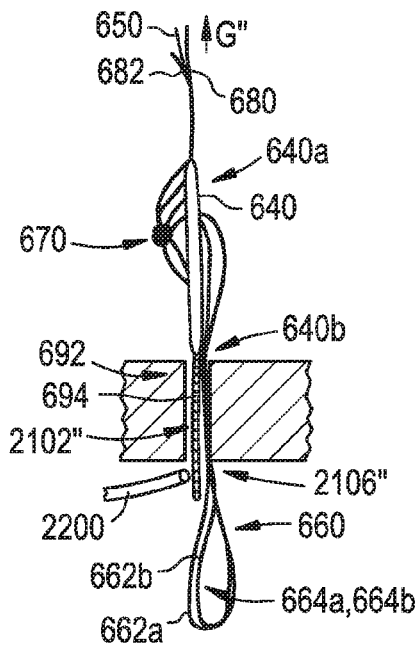
Figure 18E:
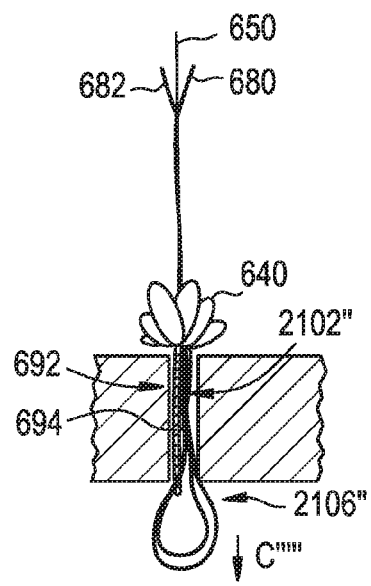

FIGS. 17-18E illustrate another alternative feedback unit 692 for use with an implant 620. The feedback unit 692 described is a measuring tail 694 that extends from a terminal end 640b of a flexible filament body 640 of the implant 620. The measuring tail 694 includes markings 697 along its length $l_T$ that denote the distance each marking of the markings 697 is from the terminal end 640b of the flexible filament body 640. The inclusion of the measuring tail 694 at the terminal end 640b can be particularly useful for embodiments in which an opposed terminal end 640a includes a leading tail 650. The measuring tail 694 can be flexible such that it can easily pass through a bone tunnel 2100'', e.g., a femoral tunnel, including both an implant passing tunnel 2102'' and a graft tunnel 2106'' (FIGS. 18A-18E), and it can be made from the same filament that forms the flexible filament body 640, or it can be a different filament or other flexible material. The length of the measuring tail 694 is typically at least as long as a length of the implant-passing tunnel 2102'' so that way the tail 694 can help provide information to the surgeon about whether the flexible filament body 640 has passed through the implant-passing tunnel 2102", as described below. A width of the measuring tail 694 can be such that it is skinny enough to be able to pass through the implant-passing tunnel 2102". In the illustrated embodiment, the measuring tail is approximately 20 millimeters long and includes markings 697 on a surface thereof in 5 millimeter increments, starting from 0 millimeters and going to 20 millimeters. Any number and increment of markings 697 can be used. In some embodiments, the tail 694 can be color coded or include other visualization features that help make it easier for a surgeon to see the markings on the body.

In use, the implant 620 can include the flexible filament body 640 and a suture filament or repair construct 660 associated with the body 640 and formed into coils 662a, 662b. A graft 690 can be disposed within openings 664a, 664b of the coils 662a, 662b, and thus associated with the body 640, as shown in FIG. 18A. The flexible filament body 640 includes the leading tail 650, and the suture filament 660 includes a slidable portion 670 disposed on a first side 642 of the body 640 having closure limbs or tensioning tails 680, 682 extending therefrom, and a majority of the coils 662a, 662b are disposed on a second side 644 of the body 640. Prior to implantation, a length of the implant-passing tunnel 2102" of the bone tunnel 2100" can be measured, and the measured length marked on the measuring tail 694.

The implant 620 can be drawn into the graft tunnel 2106" and the implant-passing tunnel 2102" by applying tension to the leading end approximately in a direction G" as illustrated in FIG. 18A. A length of the implant-tunnel 2102" can be less than or equal to the length of the measuring tail 694. The flexible filament body 640 then passes through the graft tunnel 2106", as shown in FIG. 18B, and into the implant-passing tunnel 2102", as shown in FIG. 18C. In the illustrated embodiment, as the terminal end 640a of the flexible filament body 640 exits the implant-passing tunnel 2102", the measuring tail 694 begins to enter the graft-passing tunnel 2106". As shown in FIG. 18D, a visualization device 2200, such as an endoscope, can be placed proximate to a distal end of the implant-passing tunnel 2102" to allow a user to watch when the marked location on the measuring tail 694, which denotes the length of the implant-passing tunnel 2102", enters the implant-passing tunnel 2102". When that marked location enters the implant-passing tunnel 2102", a user also knows that the flexible filament body 640 is fully exiting the implant-passing tunnel 2102". After the flexible filament body 640 has fully exited the implant-passing tunnel 2102", or even before it has fully exited in some instances, the body 640 can be actuated into the anchoring configuration, as shown in FIG. 18E, using techniques already discussed herein, including by applying tension to the coils 662a, 662b in a direction away from the body 640, as shown by applying tension approximately in a direction C"". Further, a person skilled in the art will recognize that other locations can be marked on the marking tail 694, and the timing of when different portions of the implant 620, the feedback unit 692, and/or the graft 690 enter and exit portions of the bone tunnel 2100" can be changed and adjusted as desired without departing from the spirit of the present disclosure.

Figure 19A:
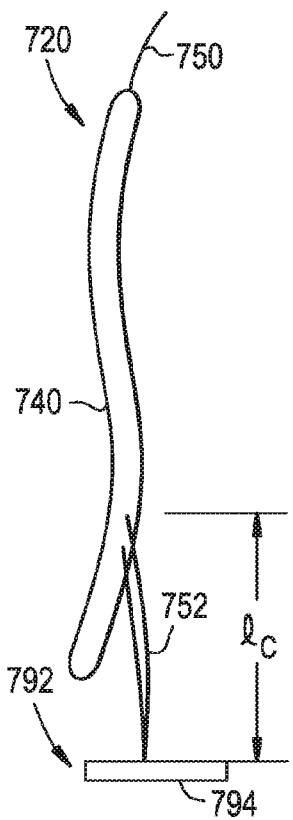
FIG. 19A is a side view of one exemplary embodiment of a surgical implant having an exemplary embodiment of a feedback unit extending distally beyond a distal end of the implant.

FIGS. 19A-20E illustrate still another alternative feedback unit 792 for use with an implant 720. The feedback unit 792 is a rigid body 794 having a length $l_B$ that is larger than a diameter of an implant-passing tunnel 2102''' so that the unit 792 cannot pass into the implant-passing tunnel 2102'''. The rigid body 794 can have any number of shapes, similar to the pledgets 594 of FIGS. 15A-15E, but in the illustrated embodiment the body 794 is a disk or puck shape. As shown in FIGS. 19A and 19B, the body 794 is attached to a flexible filament body 740 of the implant 720 using a connecting filament 752, and a length $l_C$ of the connecting filament 752 is as long as, or slightly longer, than a length of the implant-passing tunnel 2102'''. As a result, the body 794 can engage bone proximate to a distal end of the implant-passing tunnel 2102''' while the flexible filament body 740 can exit a proximal end of the implant-passing tunnel 2102''', and the connecting filament 752 extending therebetween remains disposed in the implant-passing tunnel 2102'''. Engagement of the bone proximate to the distal end of the implant-passing tunnel 2102''' provides both audible and tactile feedback to the user.

Figure 19B:
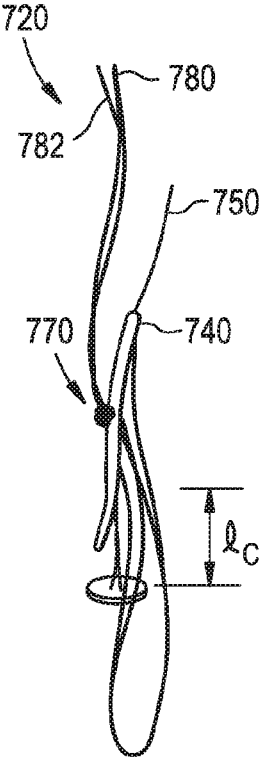
FIG. 19B is a side view of the implant of FIG. 19A, the implant having a suture filament passing through a filament body.

FIG. 19B illustrates that the implant 720 can also include a suture filament or repair construct 760 associated with the flexible filament body 740 using techniques provided for herein or otherwise known to those skilled in the art. In the illustrated embodiment, the repair construct 760 includes coils 762a, 762b that extend freely from the flexible filament body 740 and are not coupled with or directly associated with the body 740. In other embodiments, one or more portions of the repair construct 760 can be passed through the body 740. Further, a leading tail 750 can also be associated with the flexible filament body 740, and a graft 790 can be disposed within openings 764a, 764b of the coils 762a, 762b, as shown in FIGS. 20A-20E. The repair construct 760 can also include a slidable portion 770 disposed on a first side 742 of the body 740 having closure limbs or tensioning tails 780, 782 extending therefrom, and a majority of the coils 762a, 762b can be disposed on a second side 744 of the body 740.

Figure 20A:
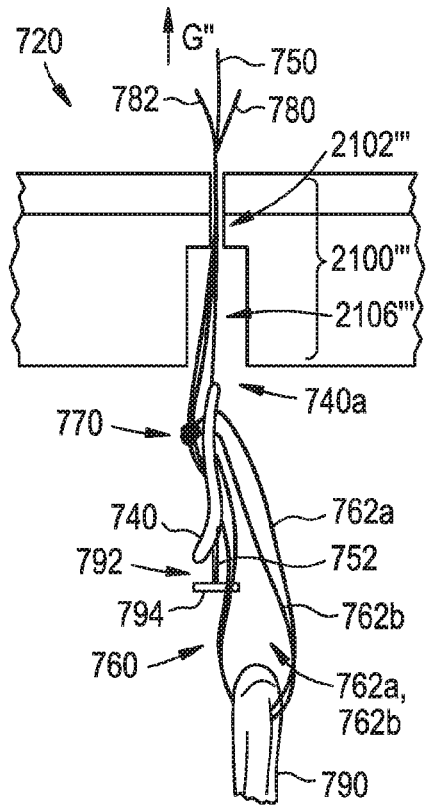
FIGS. 20A-20E are sequential, schematic, side, cross-sectional views of one exemplary embodiment for using the surgical implant of FIG. 19B in conjunction with an ACL repair.
Figure 20B:
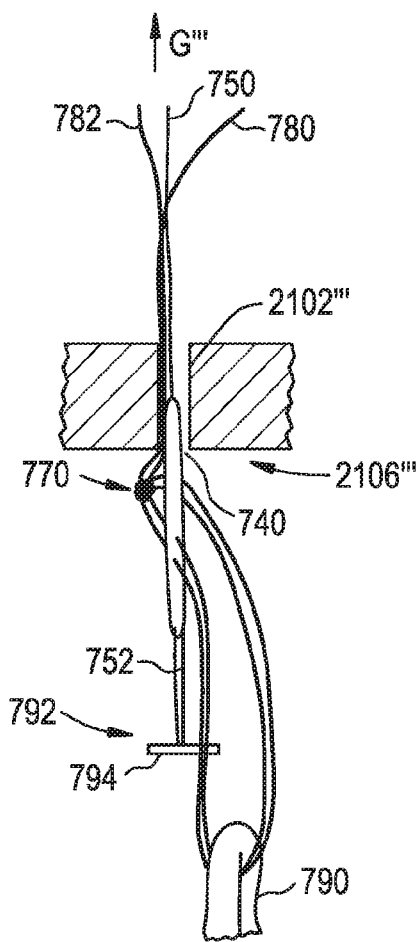
Figure 20C:
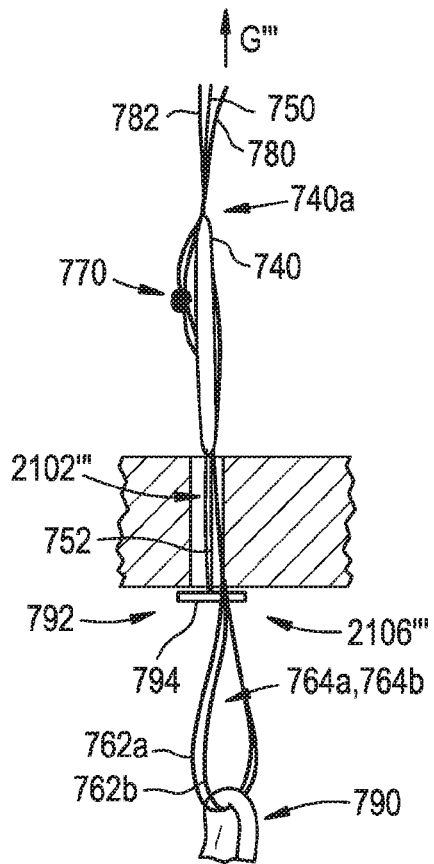

In use, the implant 720 can be drawn into a bone tunnel 2100''' having both an implant-passing tunnel 2102''' and a graft tunnel 2106''' by applying tension to the leading tail 750 approximately in a direction G''' as illustrated in FIG. 20A. The flexible filament body 740 then passes through the graft tunnel 2106''' and into the implant-passing tunnel 2102''', as shown in FIG. 20B. As a terminal end 740a of the flexible filament body 740 approaches the proximal end of the implant-passing tunnel 2102''', the body 794 engages bone surrounding a distal end of the implant-passing tunnel 2102'''. As shown in FIG. 20C, in embodiments in which the repair construct 760 is not passed through the body 794, the repair construct 760 can wrap around an outer perimeter of the body 794 as it passes from one side 742 of the body 740 to the opposite side 744, and into the graft tunnel 2106'''. Thus, the body 794 may engage the bone directly, or it may have a repair construct 760 disposed therebetween. The body 794 can have a smooth surface to prevent the body 794 from undesirably cutting or causing the repair construct 760 to fray when the repair construct 760 is pinched between the body 794 and the bone. In alternative embodiments, the repair construct 760 can pass through the body 794, in which case the body 794 can directly engage the bone.

Figure 20D:
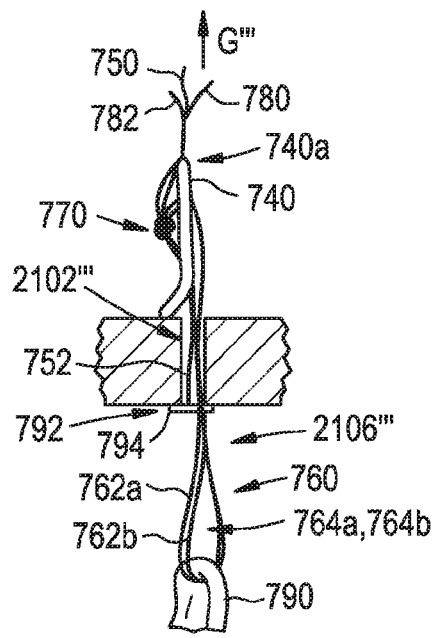
Figure 20E:
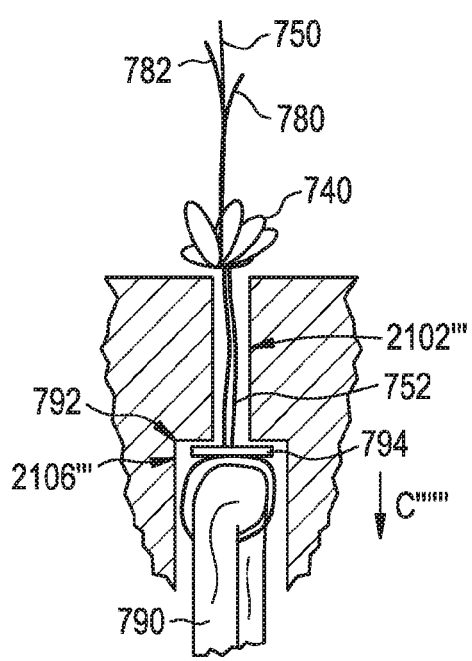

Further application of tension to the leading tail 750 approximately in the direction G''' can pull any remaining portion of the flexible filament body 740 out of the implant-passing tunnel 2102''', as shown in FIG. 20D. The body 794 remains disposed at the distal end of the implant-passing tunnel 2102''' because the body 794 remains engaged with the bone. Likewise, the repair construct 760 remains disposed in both the implant-passing and graft tunnels 2102''', 2106''', and the graft 790 remains below the implant-passing tunnel 2102''', because the body 794 prevents further advancement through the tunnel 2102'''. Similar to other embodiments, the flexible filament body 740 can then be actuated, as shown in FIG. 20E, to set the location of the flexible filament body 740 with respect to bone when the body 740 is in the anchoring configuration. Actuation can be performed using techniques already discussed herein, including by applying tension to the coils 762a, 762b in a direction away from the body 740, as shown by applying tension approximately in a direction C''''. The repair construct 760 can be manipulated to decrease a size of the openings 764a, 764b of the coils 762a, 762b to pull the graft 790 into, or further into, the graft tunnel 2106''', using techniques provided for herein or otherwise known to those skilled in the art. As shown in FIG. 20E, the graft 790 can be pulled up to the body 794 while the flexible filament body 740 is anchored with respect to the tunnel 2100''' at the proximal end of the implant-passing tunnel 2102'''.

Exemplary size and shapes of the various embodiments of feedback units can depend on a variety of factors, including but not limited to the sizes and shapes of the other components with which it is used (e.g., the implants, flexible filament bodies, repair constructs, grafts), the type of procedure being performed, and preferences of the user. In some exemplary embodiments, a material used to form the bodies 494, 594, 594', 594'', 594''', 594'''', 694, and 794 includes but is not limited to biocompatible materials, polymers, plastics, polyetheretherketone (PEEK), ultra high molecular weight polyethylene, and polypropylene. More than one of these materials can be used to form a feedback unit.

Figure 21A:
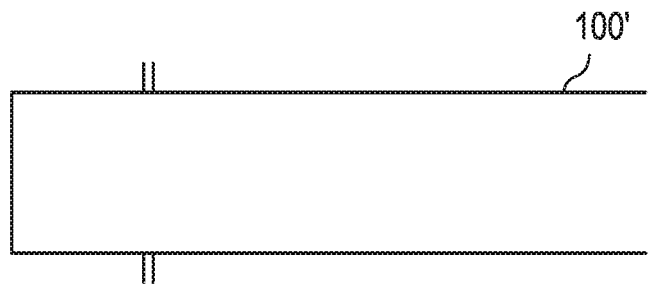
FIGS. 21A-21C are sequential, schematic, side, cross-sectional views of a method for forming a bone tunnel in a bone for use in conjunction with an ACL repair in view of the various surgical implants provided for herein or derivable from the present disclosures.
Figure 21B:
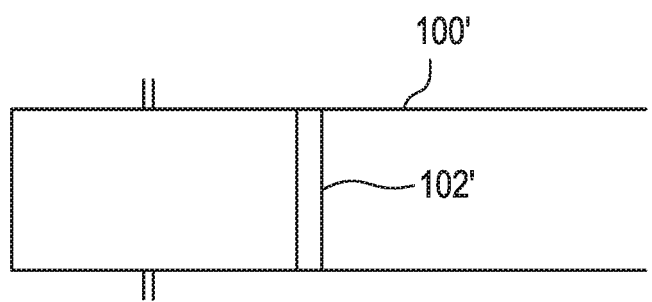
Figure 21C:
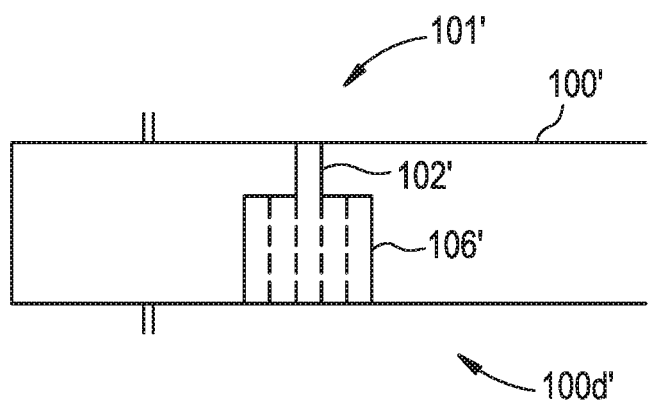

FIGS. 21A-21C illustrate one exemplary embodiment for forming a tunnel 101' (FIG. 21C), e.g., a femoral tunnel, in bone 100' through which implants of the nature provided for herein, or otherwise derivable from the disclosures herein, can be used. The bone 100' in which the tunnel 101' is to be formed is illustrated in FIG. 21A. The procedure begins by using a Beath pin to form a tunnel 102' through an entire thickness of the bone 100', as shown in FIG. 21B, the tunnel 102' having a diameter approximately in the range of about 2 millimeters to about 2.5 millimeters. The Beath pin, which is typically thin and long, can remain disposed within the bone tunnel 102' to act as a guidewire to help position additional tools for drilling the portion of the tunnel 101' having a larger diameter.

More particularly, a reamer can be passed over the Beath pin from a distal end of the bone 100d' to form a larger portion of the tunnel 101', shown in FIG. 21C. A diameter of the larger portion can be based on the size of the graft(s) to be disposed therein, and can be approximately in the range of about 6 millimeters to about 8 millimeters. As described above, the first, proximal portion 102' of the tunnel 101' illustrated in FIG. 21C serves as the implant-passing tunnel, and the second, distal portion of the tunnel 106' illustrated in FIG. 21C serves as the graft tunnel. In comparison to the method of forming bone tunnels 101 described with respect to FIGS. 1A-1D, the methods provided for as described with respect to FIGS. 21A-21C eliminate a drilling step and remove less bone because no expansion of the top portion of the tunnel is required in view of the implants and methods disclosed herein.

One skilled in the art will appreciate further features and advantages of the invention based on the above-described embodiments. Accordingly, the invention is not to be limited by what has been particularly shown and described, except as indicated by the appended claims. For example, to the extent the present disclosure disclose using the devices and methods provided for herein for ACL repairs and/or within a femoral tunnel, a person skilled in the art will recognize how the present disclosures can be adapted for use with other anatomies. All publications and references cited herein are expressly incorporated herein by reference in their entirety.

What is claimed is:

1. A surgical implant, comprising:
   a flexible filament body;
   a suture filament extending through the flexible filament body at two or more separate locations on the flexible filament body to form one or more coils such that a portion of each coil is disposed on a top side of the body and a portion of each coil is disposed on a bottom side of the body with each coil defining an opening thereof, the suture filament also having a slidable knot formed therefrom such that movement of the slidable knot towards and away from the flexible filament body causes a size of at least one opening of the one or more coils to change, and a tensioning tail that extends from the slidable knot and is configured to move the slidable knot when tension is applied to the tensioning tail, changing the size of the at least one opening of the one or more coils, the tensioning tail extending from one side of the slidable knot and the one or more coils extending from an opposite side of the knot, and a first location and a second location of the two or more separate locations on the flexible filament body being located on opposed sides of the flexible filament body along a length of the body, with the slidable knot of the suture filament being disposed at a location that is axial to a point positioned longitudinally along the suture filament between the first and second locations;
   wherein the flexible filament body and suture filament are configured so application of tension to the one or more coils in a direction away from the flexible filament body causes the flexible filament body to constrict such that the first and second locations on the flexible filament body are located closer together than they were prior to the flexible filament body constricting when the flexible filament body is extended along its length.

2. The implant of claim 1, wherein the slidable knot is a self-locking knot.

3. The implant of claim 1, wherein the suture filament includes a hollow portion, and the slidable knot comprises a portion of the suture filament being disposed within the hollow portion, the portion of the suture filament disposed within the hollow portion being adjustable by applying tension to the tensioning tail.

4. The implant of claim 3, wherein the suture filament includes a second hollow portion and a sliding portion, the sliding portion comprising a portion of the suture filament being disposed within the second hollow portion, the portion of the suture filament disposed within the second hollow portion being adjustable by applying tension to a second tensioning tail formed from the suture filament, the second tensioning tail extending from the sliding portion and being configured to move the sliding portion to change the size of at least one opening of the one or more coils.

5. The implant of claim 1, wherein a distance extending between terminal, lengthwise ends of the flexible filament body as measured prior to being constricted when the flexible filament body is extended along its length is greater than a distance extending between terminal, lengthwise ends of the flexible filament body as measured after the flexible filament body is constricted.

6. The implant of claim 1, further comprising a pliable feedback unit disposed in a portion of the flexible filament body, the feedback unit being configured to produce at least one of an audible sound and tactile feedback when it moves from a bent configuration to a straight configuration.

7. The implant of claim 1, further comprising a pliable feedback unit coupled to a terminal end of the flexible filament body, the feedback unit being configured to produce at least one of an audible sound and tactile feedback when it moves from a bent configuration to a straight configuration.

8. The implant of claim 1, further comprising a feedback unit having a known length extending from a terminal end of the flexible filament body, the feedback unit providing information about a location of the flexible filament body in view of the known length of the feedback unit.

9. The implant of claim 1, further comprising a rigid feedback unit coupled to the flexible filament body by way of a connecting filament, the rigid feedback unit being configured to engage bone surrounding a tunnel to prevent the suture filament from passing through the tunnel.

10. The implant of claim 1, wherein the coils are substantially concentric.

11. The implant of claim 1, wherein the slidable knot is at a medial position relative to the flexible filament body.

12. A surgical implant, comprising:
   a filament body having an unstressed configuration with a first length extending between opposed terminal ends of the filament body;
   a suture filament extending through the filament body at two or more separate locations on the filament body to form one or more coils such that a portion of each coil is disposed on a top side of the body and a portion of each coil is disposed on a bottom side of the body with each coil defining an opening thereof, the suture filament also having a slidable portion formed therefrom such that movement of the slidable portion towards and away from the filament body causes a size of at least one opening of the one or more coils to change, the one or more coils forming a continuous closed loop; and
   a tensioning tail extending from the slidable portion and configured to move the slidable portion to change the size of the at least one opening of the one or more coils,
   wherein the filament body and the suture filament are configured such that the filament body is reconfigurable from the unstressed configuration to an anchoring configuration by application of tension to the one or more coils in a direction away from the filament body, the filament body having in the anchoring configuration a second length extending between opposed terminal ends of the reconfigured filament body with the first and second lengths being measured along a longitudinal axis of the filament body and the first length being greater than the second length.

13. The implant of claim 12, wherein the tensioning tail is formed from the suture filament.

14. The implant of claim 13, wherein the slidable portion comprises a slidable knot that is slidably adjustable by applying tension to the tensioning tail.

15. The implant of claim 14, wherein the tensioning tail extends from one side of the slidable knot and the one or more coils extend from an opposite side of the slidable knot.

16. The implant of claim 14, wherein the slidable knot is at a medial position relative to the flexible filament body.

17. The implant of claim 13, wherein the suture filament includes a hollow portion, and the slidable portion comprises a portion of the suture filament being disposed within the hollow portion, the portion of the suture filament disposed within the hollow portion being adjustable by applying tension to the tensioning tail.

18. The implant of claim 17, wherein the suture filament includes a second hollow portion and a second slidable portion, the second slidable portion comprising a portion of the suture filament being disposed within the second hollow portion, the portion of the suture filament disposed within the second hollow portion being adjustable by applying tension to a second tensioning tail formed from the suture filament, the second tensioning tail extending from the second slidable portion and being configured to move the second slidable portion to change the size of the opening of the one or more coils.

19. The implant of claim 12, further comprising a pliable feedback unit disposed in a portion of the filament body, the feedback unit being configured to produce at least one of an audible sound and tactile feedback when it moves from a bent configuration to a straight configuration.

20. The implant of claim 12, further comprising a pliable feedback unit coupled to a terminal end of the filament body, the feedback unit being configured to produce at least one of an audible sound and tactile feedback when it moves from a bent configuration to a straight configuration.

21. The implant of claim 12, further comprising a feedback unit having a known length extending from a terminal end of the filament body, the feedback unit providing information about a location of the filament body in view of the known length of the feedback unit.

22. The implant of claim 12, further comprising a rigid feedback unit coupled to the filament body by way of a connecting filament, the rigid feedback unit being configured to engage bone surrounding a tunnel to prevent the suture filament from passing through the tunnel.

23. The implant of claim 12, wherein the coils are substantially concentric.

* * * * *